US012228569B2

(12) United States Patent
Kim

(10) Patent No.: US 12,228,569 B2
(45) Date of Patent: Feb. 18, 2025

(54) BIOSENSOR

(71) Applicant: ELECTRONICS AND TELECOMMUNICATIONS RESEARCH INSTITUTE, Daejeon (KR)

(72) Inventor: Jin Tae Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 366 days.

(21) Appl. No.: 17/464,336

(22) Filed: Sep. 1, 2021

(65) Prior Publication Data

US 2022/0236262 A1 Jul. 28, 2022

(30) Foreign Application Priority Data

Jan. 26, 2021 (KR) .................. 10-2021-0010693

(51) Int. Cl.
*G01N 33/543* (2006.01)
*G01N 21/47* (2006.01)
*G01N 21/64* (2006.01)
*H01L 33/00* (2010.01)
*H01L 33/30* (2010.01)

(52) U.S. Cl.
CPC ... *G01N 33/54373* (2013.01); *G01N 21/4788* (2013.01); *G01N 21/6428* (2013.01); *H01L 33/0025* (2013.01); *H01L 33/30* (2013.01)

(58) Field of Classification Search
CPC ..... G01N 21/62–658; G01N 33/54373; G01N 21/4788; G01N 21/6428; H01L 33/0025; H01L 33/30
See application file for complete search history.

(56) References Cited

U.S. PATENT DOCUMENTS

| 5,766,956 A | * | 6/1998 | Groger ............... G01N 21/7746 422/82.11 |
| 9,196,946 B2 | | 11/2015 | Kim et al. |
| 10,408,825 B2 | | 9/2019 | Kim et al. |
| 10,625,261 B2 | | 4/2020 | Williams et al. |
| 12,099,058 B2 | | 9/2024 | Choi et al. |
| 2014/0373347 A1 | | 12/2014 | Takagi et al. |

(Continued)

FOREIGN PATENT DOCUMENTS

| CN | 105606567 A | 5/2016 |
| CN | 110632291 A | 12/2019 |

(Continued)

OTHER PUBLICATIONS

CN-105606567-A, Fu Z, G01N21/41 (Year: 2016).*

(Continued)

*Primary Examiner* — Brian J. Sines

(57) ABSTRACT

Provided is a biosensor. The biosensor includes a substrate, an optical structure provided on the substrate, and a cover provided on the substrate and having a bridge shape that is in contact with a top surface of the substrate at both sides of the optical structure. The cover has a channel extending in a first direction, the optical structure is provided inside the channel, and the optical structure is configured to capture biomaterials that travel through the channel.

16 Claims, 25 Drawing Sheets

(56) References Cited

U.S. PATENT DOCUMENTS

| | | |
|---|---|---|
| 2015/0253321 A1 | 9/2015 | Chou et al. |
| 2019/0064532 A1* | 2/2019 | Riley et al. |
| 2019/0257784 A1* | 8/2019 | Jeong ................ G01N 27/4141 |
| 2020/0114349 A1* | 4/2020 | Hu ........................ G01N 21/78 |
| 2020/0116729 A1 | 4/2020 | Irudayaraj |
| 2020/0188914 A1* | 6/2020 | Torniainen ........ B01L 3/502715 |

FOREIGN PATENT DOCUMENTS

| | | |
|---|---|---|
| JP | 2007-17282 A | 1/2007 |
| JP | 2020-38160 A | 3/2020 |
| KR | 10-0972391 B1 | 7/2010 |
| KR | 10-2019-0087982 A | 7/2019 |

OTHER PUBLICATIONS

"Advanced Topics in Lightwave Communications Generation of Optical Signals." PhD diss., Keang-Po Ho. (Year: 2005).*
"Surface plasmon resonance and immunosensors", Electronics Letters, vol. 20, Nov. 8, 1984, pp. 968-970, University college London.

* cited by examiner

BIOSENSOR

CROSS-REFERENCE TO RELATED APPLICATIONS

This U.S. non-provisional patent application claims priority under 35 U.S.C. § 119 of Korean Patent Application No. 10-2021-0010693, filed on Jan. 26, 2021, the entire contents of which are hereby incorporated by reference.

BACKGROUND

The present disclosure herein relates to a biosensor, and more particularly, to an optical biosensor including a precise nano-optical structure having a small size.

A biosensor is a sensor that is constituted by a biomaterial and a signal detection part to detect a material to be analyzed. The bio-sensing material may be an enzyme, antibodies, DNAs, etc. that are capable of selectively reacting to be bound with a specific material. The signal detection part detects a signal of the biomaterial by using various physicochemical methods such as minute electrical changes (voltage, current, resistance, etc.) depending on the presence or absence of biomaterials, changes in fluorescence intensity due to chemical reactions, and changes in optical spectrum. The biosensor is applied in the medical fields, the environmental fields, and the analysis of infectious pathogens, and the fields of application of the biosensor are very wide in ranging to sensors for military, industry, and research.

The optical biosensor uses a method of analyzing the presence or absence of the biomaterial by converting an optical signal emitted from the biomaterial into an electrical signal by using a light emitting device and a photodetector. As the optical method for detecting the biomaterials, mainly, a labeling biosensor, in which an antibody is labeled with a fluorescent material, etc., to detect a corresponding antigen, thereby implementing quantification of the antigen to be analyzed in proportion to the intensity of the fluorescence measured from the biosensor is widely used.

SUMMARY

The present disclosure provides a biosensor including a precise nano-optical structure having a small size.

Technical objects to be solved by the present invention are not limited to the aforementioned technical objects and unmentioned technical objects will be clearly understood by those skilled in the art from the specification and the appended claims.

An embodiment of the inventive concept provides a biosensor including: a substrate; an optical structure provided on the substrate; and a cover provided on the substrate and having a bridge shape that is in contact with a top surface of the substrate at both sides of the optical structure, wherein the cover has a channel extending in a first direction, the optical structure is provided inside the channel, and the optical structure is configured to capture biomaterials that travel through the channel.

In an embodiment, the optical structure may include a lower layer, an active layer, and an upper layer, which are sequentially stacked on the substrate, wherein the active layer may be interposed between the lower layer and the upper layer.

In an embodiment, the optical structure may include a Group III-V semiconductor material, the lower layer and the upper layer may include the same semiconductor material, and the active layer may include a semiconductor material different from that of each of the lower layer and the upper layer.

In an embodiment, the optical structure may have a plurality of nanoholes passing through the lower layer, the active layer, and the upper layer, the nanoholes may be arranged in the first direction and spaced apart from each other in the first direction, and a diameter and a period of each of the nanoholes may vary in the first direction.

In an embodiment, the diameter of each of the nanoholes may decrease in the first direction from one end of the optical structure toward a central portion of the optical structure and may increase in the first direction from the central portion toward the other end of the optical structure, which faces the one end.

In an embodiment, the biosensor may further include a CMOS camera or CCD camera provided on the optical structure.

In an embodiment, the optical structure may include a lower layer on the substrate and an upper layer on a partial area of the lower layer, wherein the optical structure may have a plurality of nanoholes passing through the lower layer to expose the top surface of the substrate, the nanoholes may be arranged in the first direction and spaced apart from each other in the first direction, and a diameter and a period of each of the nanoholes may vary in the first direction.

In an embodiment, the upper layer may include one of a semiconductor material or transition metal dichalcogenide, graphene, and hexagonal boron nitride (hBN).

In an embodiment, the biosensor may further include a plurality of antibodies provided on the optical structure, wherein the antibodies may be arranged along the first direction on a top surface of the optical structure, and the antibodies may be configured to capture the biomaterials that travel through the channel.

In an embodiment, the optical structure may include a plurality of meta-material unit elements having a geometric period, wherein the meta-material unit elements may be configured to diffract incident light irradiated from a bottom surface of the substrate toward the optical structure.

In an embodiment, the optical structure may be provided in plurality, and the optical structures may be arranged along the first direction and a second direction crossing the first direction.

In an embodiment of the inventive concept, a biosensor includes: a substrate; an optical structure having a bar shape extending in a first direction on the substrate; and a cover provided on the substrate and having a bridge shape that is in contact with a top surface of the substrate at both sides of the optical structure, wherein the cover has a channel extending in the first direction, the optical structure is provided inside the channel, and the optical structure includes: a lower layer on the substrate; an upper layer on the lower layer; and an active layer interposed between the lower layer and the upper layer, wherein the optical structure has a plurality of nanoholes passing through the lower layer, the active layer, and the upper layer.

In an embodiment, the active layer may have quantum dots configured to control photons of laser light emitted from the optical structure, and the active layer may include a material different from that of each of the lower layer and the upper layer.

In an embodiment, a diameter of each of the nanoholes disposed at a central portion of the optical structure may be less than that of each of the nanoholes disposed at both ends of the optical structure.

In an embodiment, the optical structure may be provided in plurality, the optical structures may be arranged along the first direction and a second direction crossing the first direction, the optical structures arranged along the first direction may be spaced apart from each other in the first direction, and sidewalls of the optical structures are aligned with each other, and the optical structures arranged along the second direction may be spaced apart from each other in the second direction, and sidewalls of the optical structures may be aligned with each other.

In an embodiment of the inventive concept, a biosensor includes: a measuring unit configured to measure an emission pattern or a diffraction pattern; a data storage unit configured to store data including the emission pattern or the diffraction pattern measured in the measuring unit; a data learning unit is configured to perform machine learning through the data transmitted from the data storage unit and determine a presence or absence of the biomaterial and/or the number of biomaterials through the data; and a display unit configured to visualize information determined by the data learning unit, wherein the measuring unit includes: a substrate; an optical structure provided on the substrate; and a cover having a bridge shape that is in contact with a top surface of the substrate at both sides of the optical structure, wherein the cover has a channel extending in a first direction, the optical structure is provided inside the channel, and the optical structure is configured to capture biomaterials that travel through the channel.

In an embodiment, the data learning unit may be trained to determine a presence or absence of the biomaterial and/or the number of biomaterials through a change in at least one of a resonance wavelength, a phase, or polarization.

In an embodiment, the optical structure may include: a lower layer on the substrate; an upper layer on the lower layer; and an active layer interposed between the lower layer and the upper layer, wherein the optical structure may have a plurality of nanoholes passing through the lower layer, the active layer, and the upper layer.

In an embodiment, the optical structure may include a plurality of meta-material unit elements having a geometric period, wherein the meta-material unit elements may be configured to diffract incident light irradiated from a bottom surface of the substrate toward the optical structure.

In an embodiment, the optical structure may be provided in plurality, and the optical structures may be arranged along the first direction and a second direction crossing the first direction.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIGS. 3A and 3B are plan and cross-sectional views for explaining the optical structure of the biosensor according to embodiments of the inventive concept, wherein FIG. 3B is a cross-sectional view taken along line I-I' of FIG. 3A;

FIGS. 10A to 17A are perspective views for explaining an operation of the biosensor according to embodiment of the inventive concept;

FIGS. 10B to 17B are pictures illustrating a diffraction pattern of the optical structure of the biosensor according to embodiments of the inventive concept.

DETAILED DESCRIPTION

Figure 1:
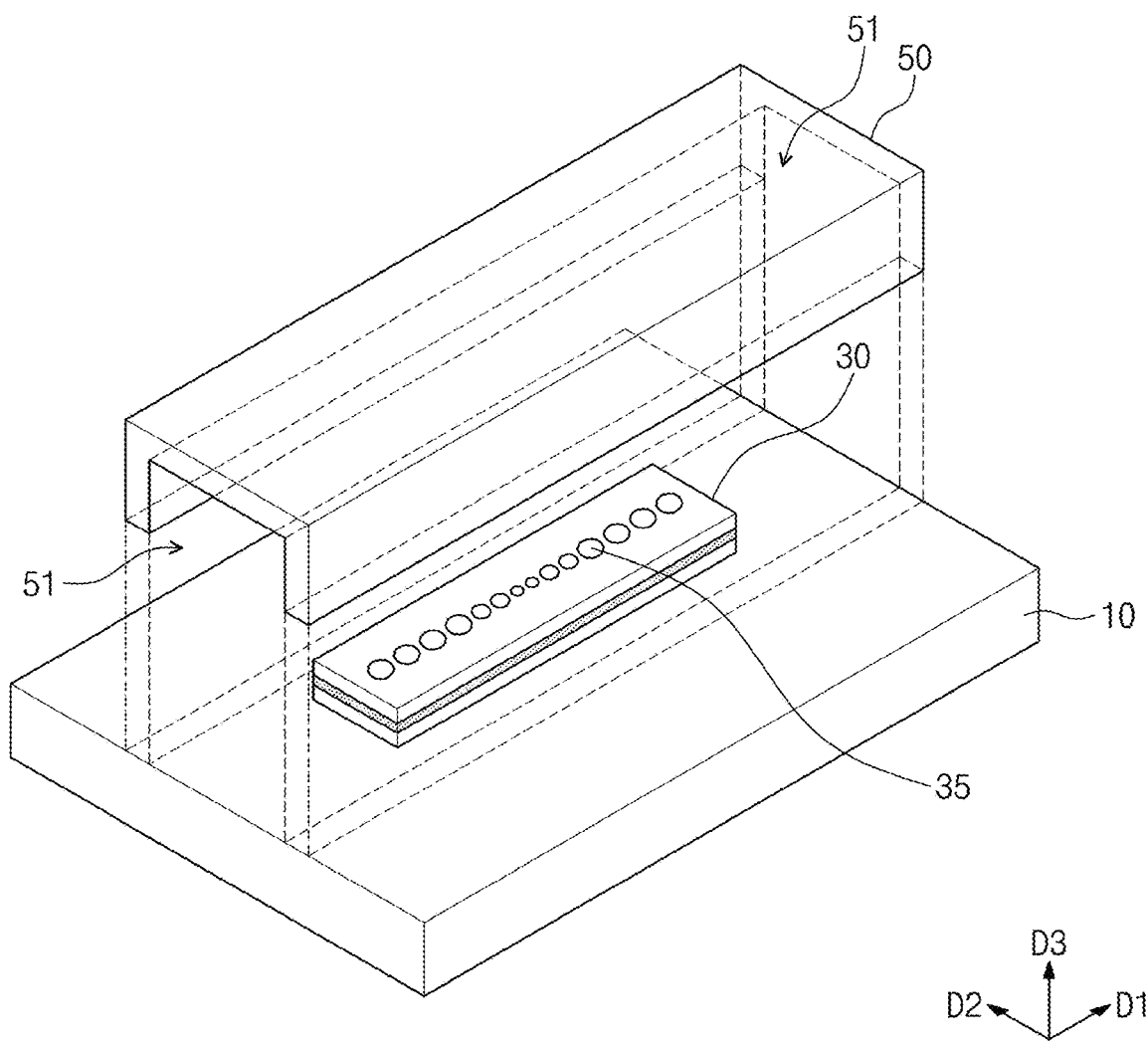
FIG. 1 is an exploded perspective view for explaining a biosensor according to embodiments of the inventive concept.

Embodiments of the inventive concept will be described with reference to the accompanying drawings so as to sufficiently understand constitutions and effects of the inventive concept.

The present invention is not limited to the embodiments disclosed below, but should be implemented in various forms, and various modifications and changes may be made. Rather, these embodiments are provided so that this disclosure will be thorough and complete, and will fully convey the scope of the present invention to those skilled in the art. Further, the present invention is only defined by scopes of claims. In the accompanying drawings, the components are shown enlarged for the sake of convenience of explanation, and the proportions of the components may be exaggerated or reduced for clarity of illustration.

In the following description, the technical terms are used only for explaining a specific exemplary embodiment while not limiting the present invention. Unless terms used in embodiments of the present invention are differently defined, the terms may be construed as meanings that are commonly known to a person skilled in the art.

In this specification, the terms of a singular form may include plural forms unless specifically mentioned. The meaning of 'comprises' and/or 'comprising' specifies a component, a step, an operation and/or an element does not exclude other components, steps, operations and/or elements.

When a layer is referred to herein as being 'on' another layer, it may be formed directly on the top of the other layer or a third layer may be interposed between them.

It will be understood that although the terms first and second are used herein to describe various regions, layers, and the like, these regions and layers should not be limited by these terms. These terms are used only to discriminate one region or layer from another region or layer. Therefore, a portion referred to as a first portion in one embodiment can be referred to as a second portion in another embodiment. An embodiment described and exemplified herein includes a complementary embodiment thereof. Like reference numerals refer to like elements throughout.

Hereinafter, embodiments of a biosensor according to the inventive concept will be described in detail with reference to the drawings.

Figure 2:
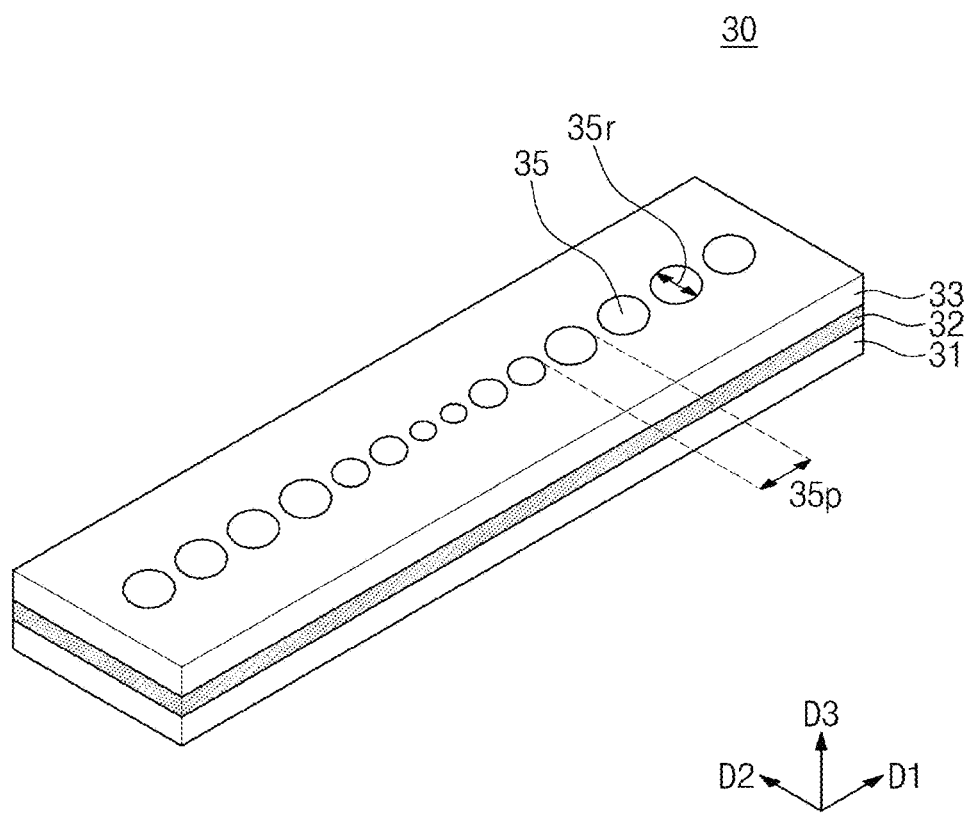
FIG. 2 is a perspective view for explaining an optical structure of the biosensor according to embodiment of the inventive concept.

FIG. 1 is an exploded perspective view for explaining the biosensor according to embodiments of the inventive concept. FIG. 2 is a perspective view for explaining an optical structure of the biosensor according to embodiment of the inventive concept.

Referring to FIGS. 1 and 2, the biosensor according to the inventive concept may include a substrate 10, an optical structure 30, and a cover 50. The substrate 10 may have a flat plate shape extending parallel to a first direction D1 and a second direction D2. A top surface of the substrate 10 may be a plane perpendicular to a third direction D3. The first direction D1 to the third direction D3 may be, for example, directions orthogonal to each other. The substrate 10 may include a material that is transparent to a wavelength of light incident into the optical structure 30 and a wavelength of light emitted from the optical structure 30.

The optical structure 30 may be provided on the substrate 10. The optical structure 30 may be, for example, a bar-shaped nano laser extending in the first direction D1. In other words, a length of the optical structure 30 in the first direction D1 may be greater than a length of the optical structure 30 in the second direction D2. The length of the optical structure 30 in the first direction D1 may be, for example, about 3 μm or more. The length of the optical structure 30 in the second direction D2 may be, for example, about 200 nm to 700 nm. A thickness of the optical structure 30 in the third direction D3 may be, for example, about 100 nm to 300 nm. However, this is merely exemplary, and the embodiment of the inventive concept is not limited thereto. For example, the optical structure 30 may have various shapes and sizes.

The optical structure 30 may include a lower layer 31, an active layer 32, and an upper layer 33, which are sequentially stacked on the substrate 10. The optical structure 30 may include, for example, Group III-V semiconductor material. The lower layer 31 and the upper layer 33 may include the same semiconductor material. The lower layer 31 and the upper layer 33 may include, for example, InP.

The active layer 32 may be interposed between the lower layer 31 and the upper layer 33. The active layer 32 may include a semiconductor material different from that of each of the lower layer 31 and the upper layer 33. The active layer 32 may include, for example, InGaAsP. The active layer 32 may have quantum dots, which may control photons of laser light emitted from the optical structure 30.

The optical structure 30 may have a plurality of nanoholes 35 passing through the lower layer 31, the active layer 32, and the upper layer 33. The nanoholes 35 may be arranged along the first direction D1 and may be spaced apart from each other in the first direction D1. A diameter 35r of each of the nanoholes 35 may be less than that of the optical structure 30 in the second direction D2. The diameter 35r of each of the nanoholes 35 may be, for example, about 100 nm to 500 nm. A top surface of each of the nanoholes 35 may have, for example, a circular shape or an elliptical shape, but the embodiment of the inventive concept is not limited thereto.

The diameter 35r and a period 35p of each of the nanoholes 35 may not be constant. The diameter 35r and the period 35p of each of the nanoholes 35 may vary in the first direction D1. For example, the diameter 35r and period 35p of each of the nanoholes 35 may decrease from one end of the optical structure 30 to a central portion of the optical structure 30 in the first direction D1, and may increase from the central portion of the optical structure 30 to the other end of the optical structure 30, which faces the one end, in the first direction D1.

The central portion of the optical structure 30 in which the nano-holes 35, each of which has a relatively small diameter 35r, are disposed may correspond a resonator region of the nano-laser. Both ends of the optical structure 30 in which the nano-holes 35, each of which has a relatively large diameter 35r, are disposed may correspond to mirror regions of the nano-laser. Specifically, when light is incident into the optical structure 30, the central portion of the optical structure 30 may generate resonance, and both the ends of the optical structure 30 may reflect the light so that the light is captured to the central portion of the structure 30 without being scattered.

The resonance wavelength at the central portion of the optical structure 30 may vary depending on the arrangement of the nanoholes 35, and the diameter 35r and/or the period 35p of each of the nanoholes 35. In addition, a quality factor of the nano-laser may vary depending on the size of the optical structure 30 and the wavelength of the incident light.

However, this is merely exemplary, and the embodiment of the inventive concept is not limited thereto. For example, the arrangement of the nanoholes 35, and the diameter 35r and/or the period 35p of each of the nanoholes 35 may be different from those shown.

The cover 50 may be provided on the substrate 10 and may have a bridge shape that is in contact with the top surface of the substrate 10 at both the sides of the optical structure 30. The cover 50 may include a material that is transparent with respect to a wavelength of light incident into the optical structure 30 and a wavelength of light emitted from the optical structure 30.

The cover 50 may have a channel 51 extending in the first direction D1. The optical structure 30 may be provided inside the channel 51. A width of the channel 51 in the first direction D1 may be greater than the length of the optical structure 30 in the first direction D1. A width of the channel 51 in the second direction D2 may be greater than or equal to the length of the optical structure 30 in the second direction D2. That is, the cover 50 may be in contact with both the side surfaces of the optical structure 30 or may be spaced apart from each other in the second direction D2. A height of the channel 51 in the third direction D3 may be greater than the thickness of the optical structure 30 in the third direction D3. That is, the cover 50 may be spaced apart from the top surface of the optical structure 30 in the third direction D3.

Figure 3A:
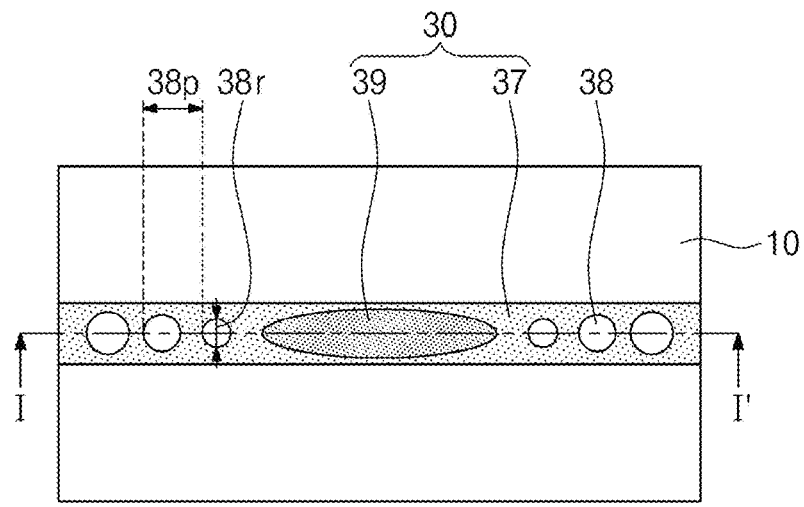
Figure 3A:
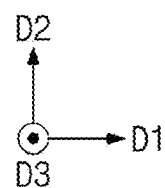
Figure 3B:
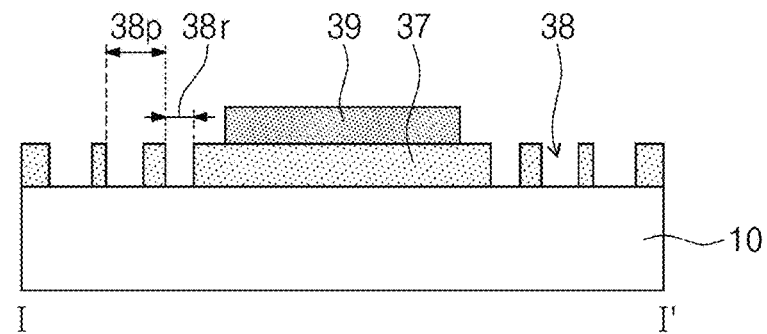
Figure 3B:
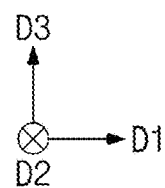

FIGS. 3A and 3B are plan and cross-sectional views for explaining the optical structure of the biosensor according to embodiments of the inventive concept, wherein FIG. 3B is a cross-sectional view taken along line I-I' of FIG. 3A.

Referring to FIGS. 3A and 3B, the optical structure 30 may include a lower layer 37 on the substrate 10 and an upper layer 39 on a partial area of the lower layer 37. A top surface of the upper layer 39 may have an elliptical or rectangular shape in which a length in the first direction D1 is greater than a length in the second direction D2, but the embodiment of the inventive concept is not limited thereto.

The substrate 10 may include, for example, silicon oxide. The lower layer 37 may include, for example, silicon. The upper layer 39 may include a two-dimensional material. The upper layer 39 may be, for example, one of a semiconductor material (e.g., InGaAsP) or transition metal dichalcogenide (e.g., MoS2, MoSe2, WS2, WSe2, MoTe2, WTe2, etc.), graphene, and hexagonal boron nitride (hBN).

The lower layer 37 may have, for example, a photonic crystal structure. The upper layer 39 may have, for example, a bound state in the continuum (BIC) structure.

The optical structure 30 may have a plurality of nanoholes 38. The nanoholes 38 may not be provided under the upper layer 39. That is, the nanoholes 38 may not overlap the upper layer 39 in the third direction D3. The nanoholes 38 may pass through the lower layer 37 to expose the top surface of the substrate 10. The nanoholes 38 may be arranged along the first direction D1 and may be spaced apart from each other in the first direction D1. A diameter 38r of each of the nanoholes 38 may be less than a length of the lower layer 37 in the second direction D2. A diameter 38r of each of the nanoholes 38 may be, for example, about 100 nm to 500 nm. A top surface of each of the nanoholes 38 may have, for example, a circular shape or an elliptical shape, but the embodiment of the inventive concept is not limited thereto.

The diameter 38r and a period 38p of each of the nanoholes 38 may not be constant. For example, the diameter 35r and period 35p of each of the nanoholes 35 may decrease from one end of the lower layer 37 to a central portion of the lower layer 37 in the first direction D1, and may increase from the central portion of the lower layer 37 to the other end of the lower layer 37, which faces the one end, in the first direction D1.

The optical structure 30 of the biosensor according to the inventive concept is not limited to that described with reference to FIGS. 2, 3A and 3B, and various planar lasers based on a semiconductor material may be used as the optical structure 30.

FIGS. 4A, 5A, 6A, and 7A are perspective views for explaining an operation of the biosensor according to embodiment of the inventive concept. FIGS. 4B, 5B, 6B, and 7B are pictures illustrating an emission pattern of the optical structure of the biosensor according to embodiments of the inventive concept.

Figure 4A:
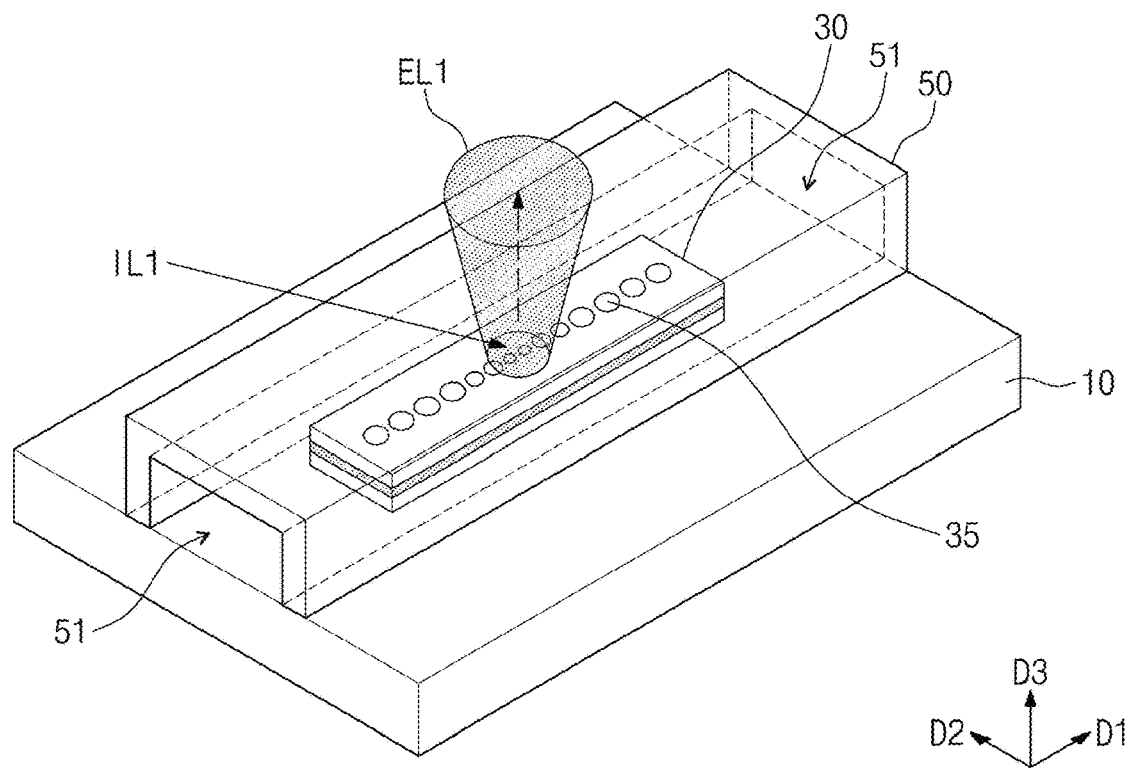
FIGS. 4A, 5A, 6A, and 7A are perspective views for explaining an operation of the biosensor according to embodiment of the inventive concept.
Figure 4B:
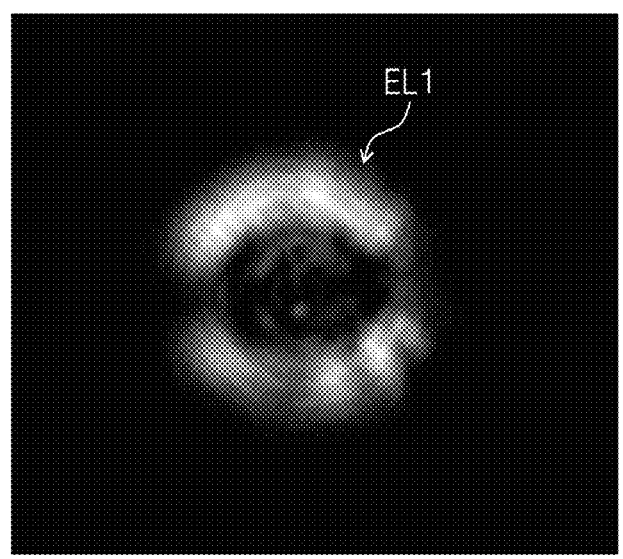
FIGS. 4B, 5B, 6B, and 7B are pictures illustrating an emission pattern of the optical structure of the biosensor according to embodiments of the inventive concept.

Referring to FIGS. 4A and 4B, first incident light IL1 may be irradiated to the central portion of the optical structure 30, and first emission light EL1 may be generated from the central portion of the optical structure 30. Although it is illustrated that the first incident light IL1 is obliquely incident on the top surface of the optical structure 30, the embodiment of the inventive concept is not limited thereto, and the first incident light IL1 may be incident at an angle different from that illustrated. The first incident light IL1 may have energy greater than an energy gap of the Group III-V semiconductor material of the optical structure 30. The first incident light IL1 may have a wavelength of, for example, a visible ray band. The optical structure 30 may generate the first emission light EL1 corresponding to the energy gap of the Group III-V semiconductor material through down conversion. The first emission light EL1 may have a wavelength of, for example, an infrared band. However, the embodiment of the inventive concept is not limited thereto, and when the optical structure 30 includes a material for adjusting the energy gap of the Group III-V semiconductor material, the first emission light EL1 may have a wavelength in the visible ray band.

The first emission light EL1 may be measured by a CMOS camera or a CCD camera on the optical structure 30, and the emission pattern of FIG. 4B represents the first emission light EL1. Hereinafter, for convenience of description, descriptions of the contents that are substantially the same as those described with reference to FIGS. 4A and 4B will be omitted, and differences will be described in detail.

Figure 5A:
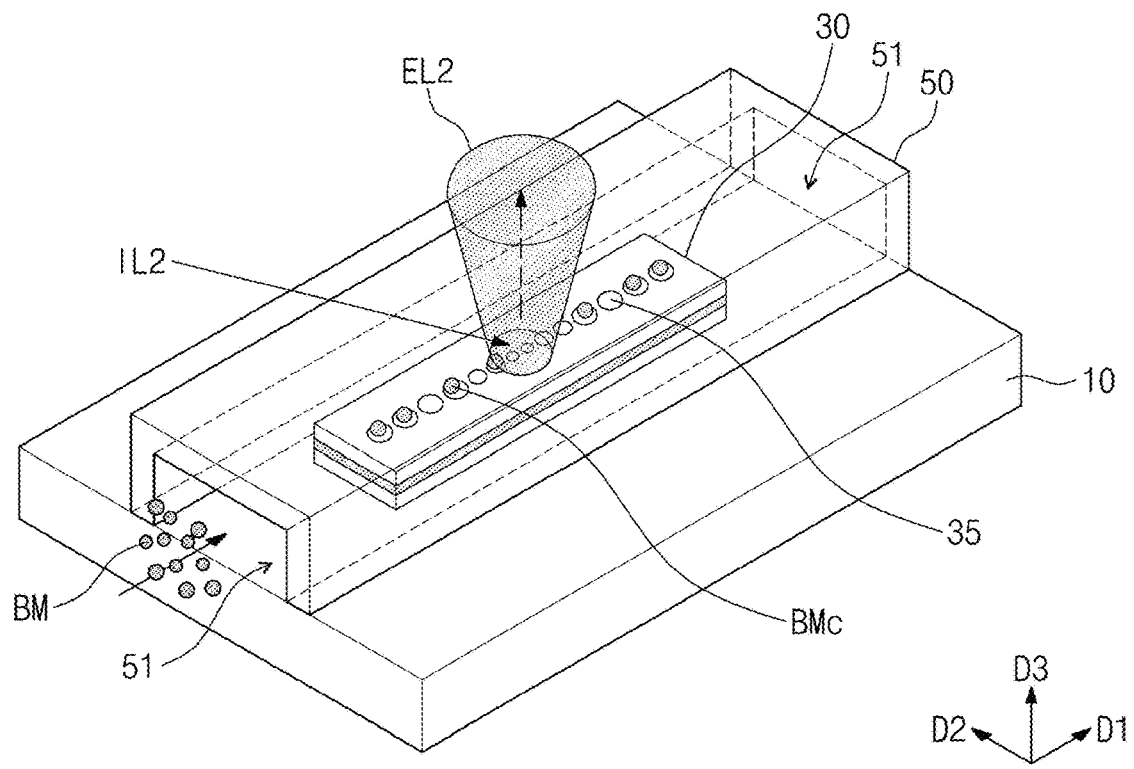
Figure 5B:
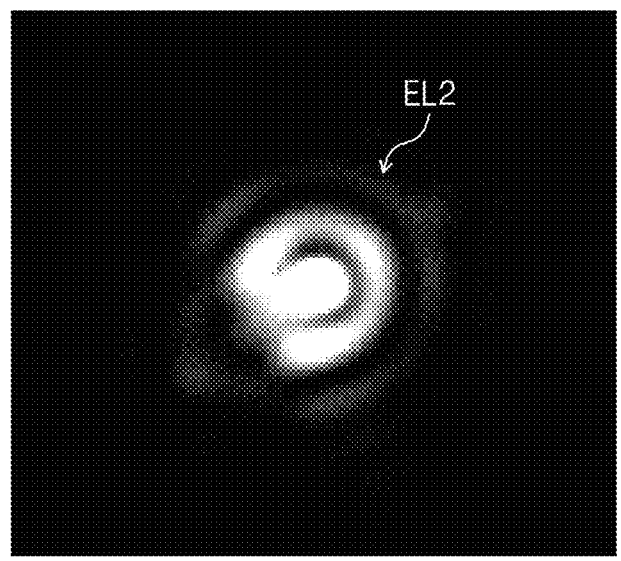

Referring to FIGS. 5A and 5B, a fluid including biomaterials BM may travel in the first direction D1 through the channel 51 of the cover 50. The biomaterials BM may include, for example, proteins, disease diagnosis-related biomarkers, viruses, bacteria, and the like. At least some of the biomaterials BM may be captured in the nanoholes 35 of the optical structure 30.

Thereafter, second incident light IL2 may be irradiated to the central portion of the optical structure 30, and second emission light EL2 may be generated from the central portion of the optical structure 30. The second incident light IL2 may have substantially the same wavelength and intensity as the first incident light IL1.

Due to the biomaterials BM captured in the nanoholes 35, the second emission light EL2 may have a wavelength and intensity different from those of the first emission light EL1. Thus, an emission pattern (an emission pattern of the second emission light EL2) of FIG. 5B may be different from the emission pattern (the emission pattern of the first emission light EL1) of FIG. 4B.

Figure 6A:
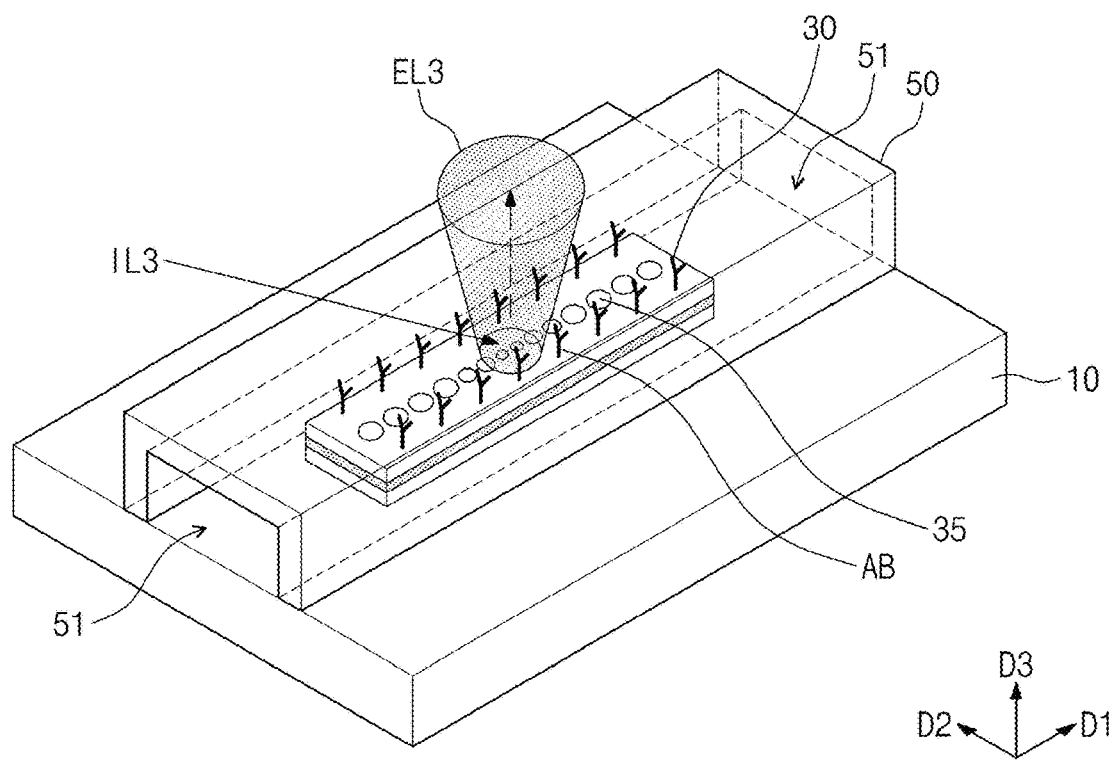
Figure 6B:
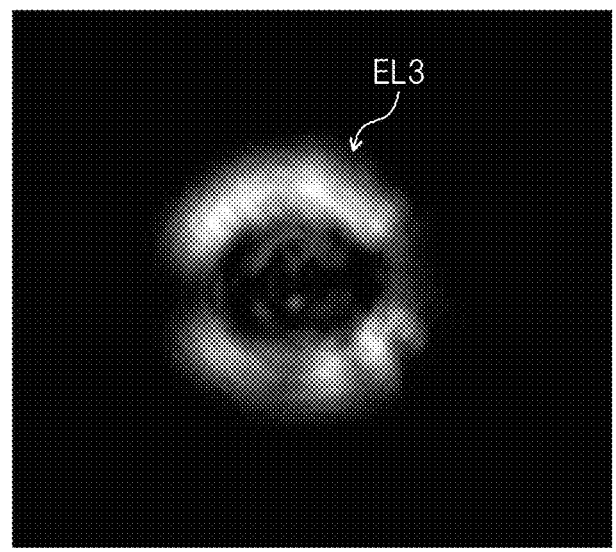

Referring to FIGS. 6A and 6B, the biosensor according to the inventive concept may further include a plurality of antibodies AB provided on the optical structure 30. The antibodies AB may be arranged along the first direction D1 on the top surface of the optical structure 30 and may be spaced apart from each other in the first direction D1. For example, the antibodies AB may be arranged in two rows on the top surface of the optical structure 30, and the rows may be spaced apart from each other in the second direction D2. Each of the antibodies AB may have, for example, a Y-shape.

Third incident light IL3 may be irradiated to the central portion of the optical structure 30 provided with the antibodies AB on the top surface thereof, and third emitted light EL3 may be generated from the central portion of the optical structure 30. The third incident light IL3 may have substantially the same wavelength and intensity as each of the first and second incident lights IL1 and IL2. The third emission light EL3 may have a wavelength and intensity similar to that of the first emission light EL1. An emission pattern (an emission pattern of the third emission light EL3) of FIG. 6B may be similar to the emission pattern (the emission pattern of the first emission light EL1) of FIG. 4B.

Figure 7A:
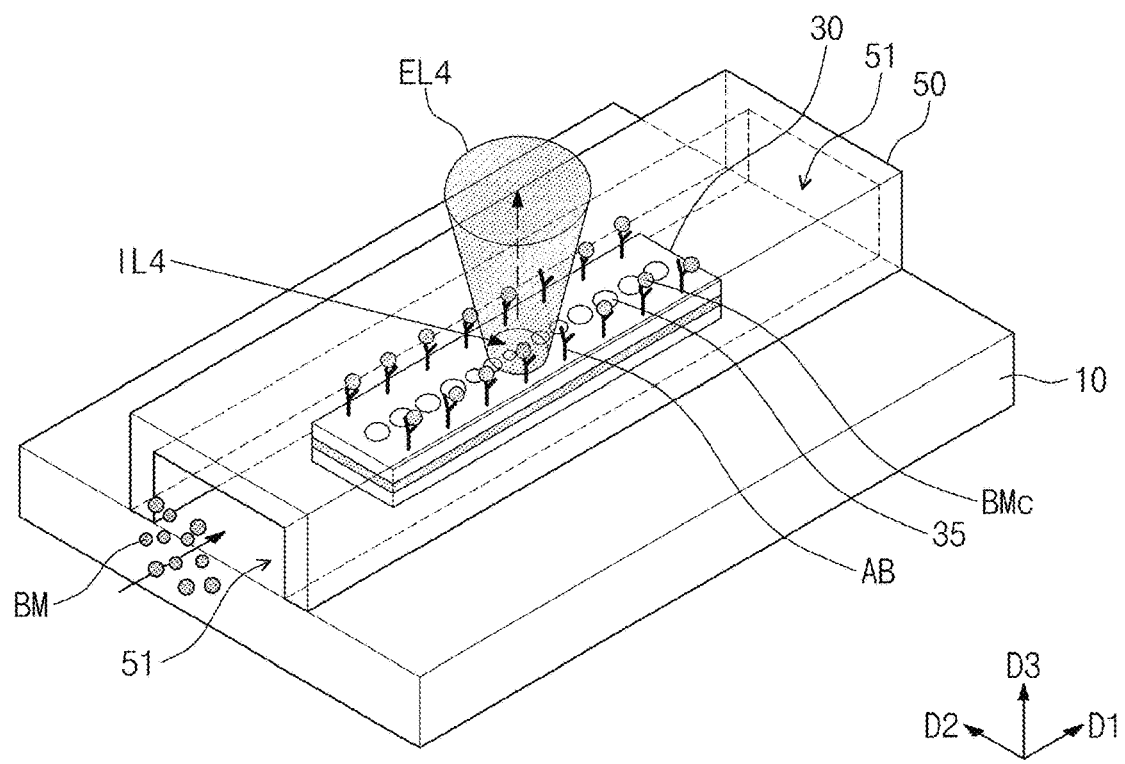
Figure 7B:
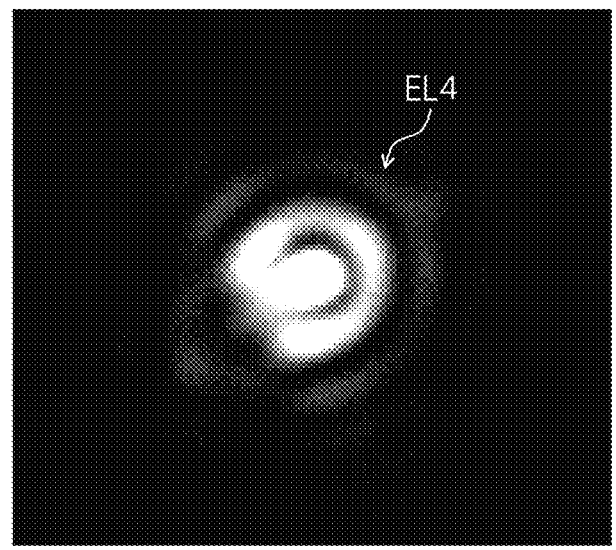

Referring to FIGS. 7A and 7B, a fluid including biomaterials BM may travel in the first direction D1 through the channel 51 of the cover 50. At least some of the biomaterials BM may be captured on the antibodies AB on the optical structure 30 (or in the nanoholes 35 of the optical structure 30).

Thereafter, fourth incident light IL4 may be irradiated to the central portion of the optical structure 30, and fourth emission light EL4 may be generated from the central portion of the optical structure 30. The fourth incident light IL4 may have substantially the same wavelength and intensity as each of the first to third incident light IL1, IL2, and IL3.

Due to the biomaterials BM captured on the antibodies AB (or in the nanoholes 35), the fourth emission light EL4 may have a wavelength and intensity different from those of the third emission light EL3. Thus, an emission pattern (the emission pattern of the fourth emission light EL4) of FIG. 7B may be different from the emission pattern (the emission pattern of the third emission light EL3) of FIG. 6B.

Figure 8:
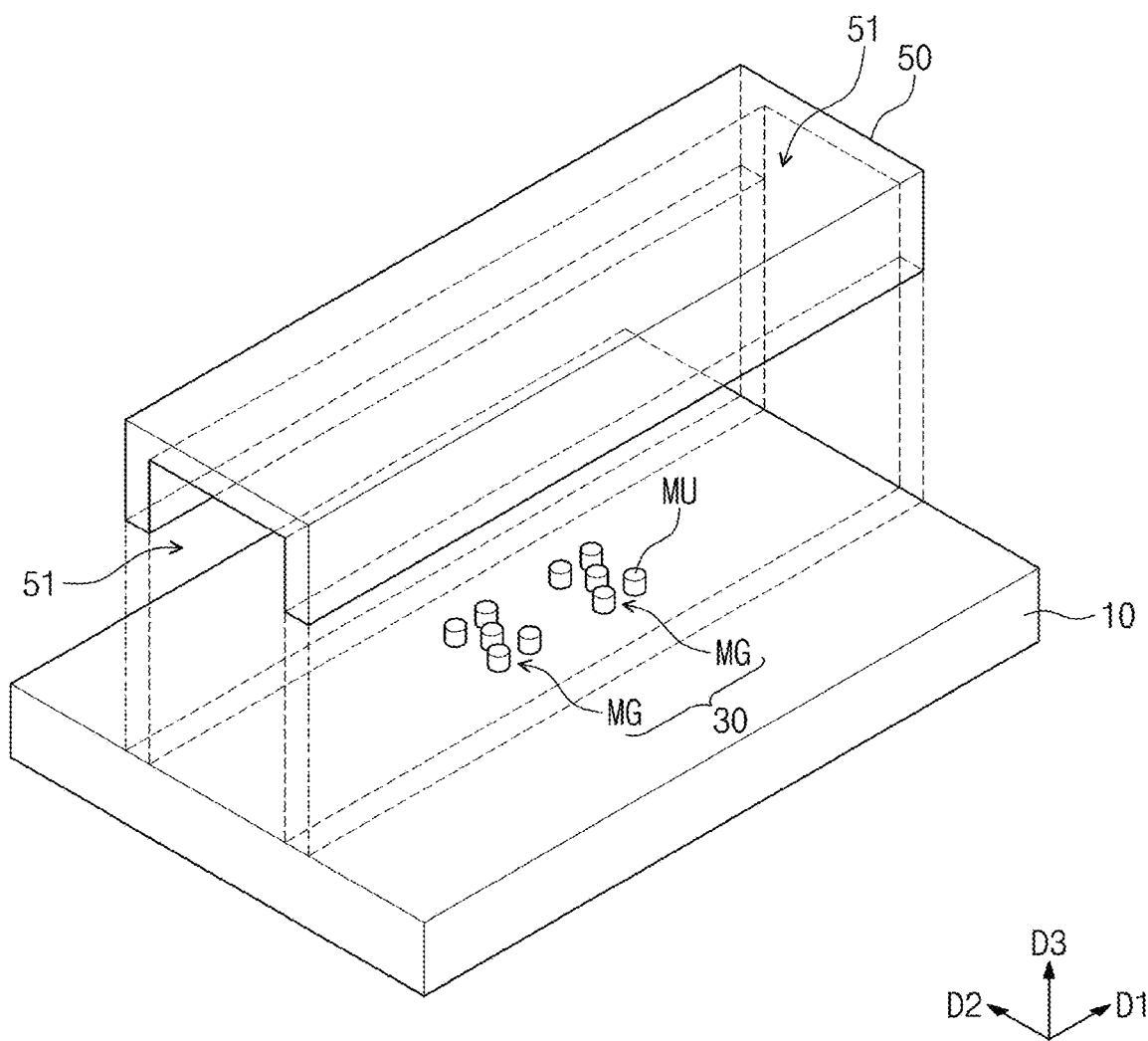
FIG. 8 is an exploded perspective view for explaining a biosensor according to embodiments of the inventive concept.

FIG. 8 is an exploded perspective view for explaining a biosensor according to embodiments of the inventive concept. Hereinafter, for convenience of description, descriptions of the contents that are substantially the same as those described with reference to FIGS. 1 and 2 will be omitted, and differences will be described in detail.

Referring to FIG. 8, a biosensor according to the inventive concept may include a substrate 10, an optical structure 30, and a cover 50. The optical structure 30 may include a plurality of meta-material groups MG, and each meta-material group MG may include a plurality of meta-material unit elements MU having a geometric period. The plurality of meta-material unit elements MU may be arranged with a specific period in each meta-material group MG. As used herein, the term 'meta-material' refers to a structure having a geometric period designed using existing materials rather than a specific material, and a plane on which the meta-material is provided may be referred to as a 'meta-surface'.

A top surface of each of the meta-material unit elements MU may have, for example, a circular shape or an elliptical shape, but the embodiment of the inventive concept is not limited thereto. For example, the top surface of each of the meta-material unit elements MU may have various shapes as described with reference to FIGS. 9A to 9H.

FIGS. 9A to 9H are plan views for explaining an optical structure of the biosensor according to embodiments of the inventive concept. Specifically, FIGS. 9A to 9H illustrate top surfaces of the meta-material group MG or the meta-material unit element MU of the optical structure described with reference to FIG. 8.

Figure 9A:
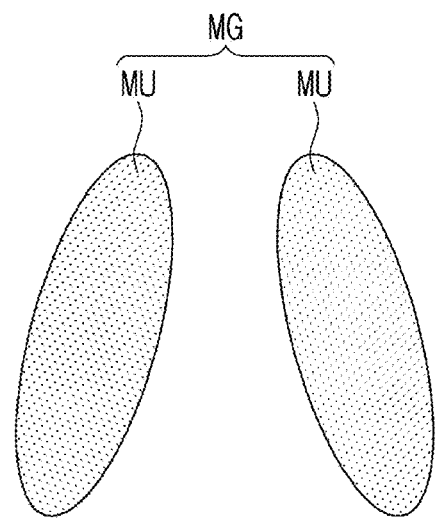
FIGS. 9A to 9H are plan views for explaining an optical structure of the biosensor according to embodiments of the inventive concept.

Referring to FIG. 9A, the meta-material group MG may include two meta-material unit elements MU. A top surface of each of the meta-material unit elements MU may have, for example, an elliptical shape. The meta-material unit elements MU of the meta-material group MG may be disposed bilaterally symmetrically.

Figure 9B:
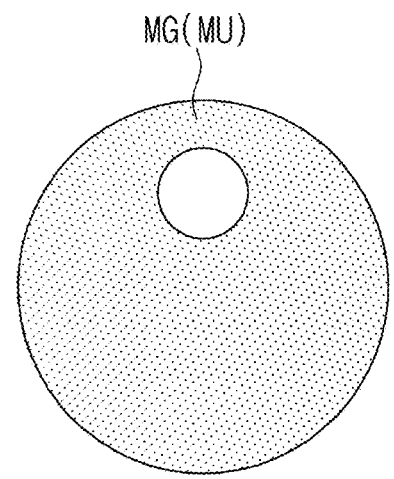
Figure 9C:
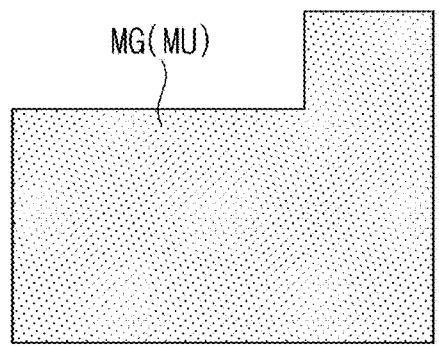

Referring to FIGS. 9B and 9C, the meta-material group MG may include one meta-material unit element MU. Referring to FIG. 9B, the top surface of the meta-material unit element MU may have, for example, a donut shape with a hole therein. The hole may be disposed at a center of the meta-material unit element MU or may be disposed close to an edge. The hole may have a circular shape, an elliptical shape or a polygonal shape.

Referring to FIG. 9C, the top surface of the meta-material unit element MU may have a polygonal shape. The top surface of the meta-material unit element MU may have, for example, a concave polygonal shape in which at least one interior angle is in a range of 180 degrees and 360 degrees, but the embodiment of the inventive concept is not limited thereto. For example, the top surface of the meta-material unit element MU may have a convex polygonal shape.

Figure 9D:
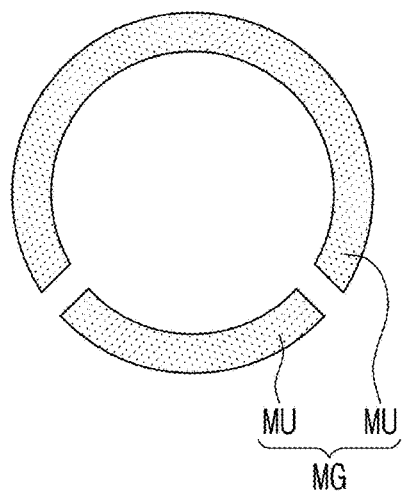
Figure 9E:
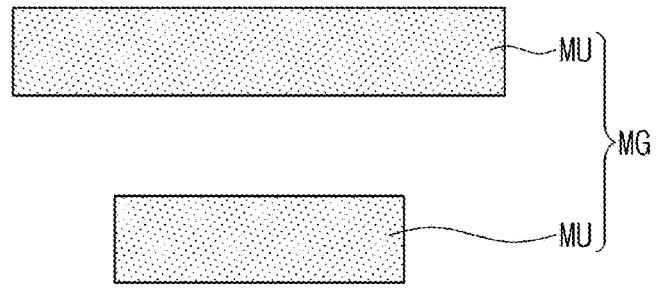
Figure 9F:
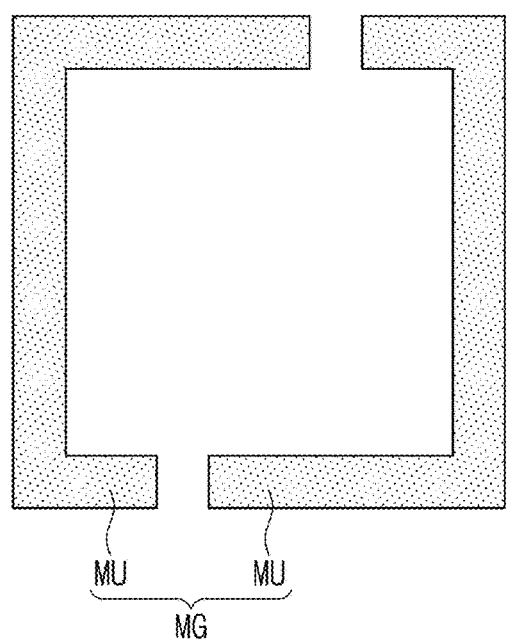

Referring to FIGS. 9D and 9E, the meta-material group MG may include two meta-material unit elements MU. Referring to FIG. 9D, a top surface of each of the meta-material unit elements MU may have, for example, an arc shape. The meta-material unit elements MU may have different sizes and/or lengths.

Referring to FIG. 9E, the top surface of each of the meta-material unit elements MU may have, for example, a rectangular shape, and the meta-material unit elements MU may extend in parallel with each other. The meta-material unit elements MU may have different sizes and/or lengths.

Figure 9G:
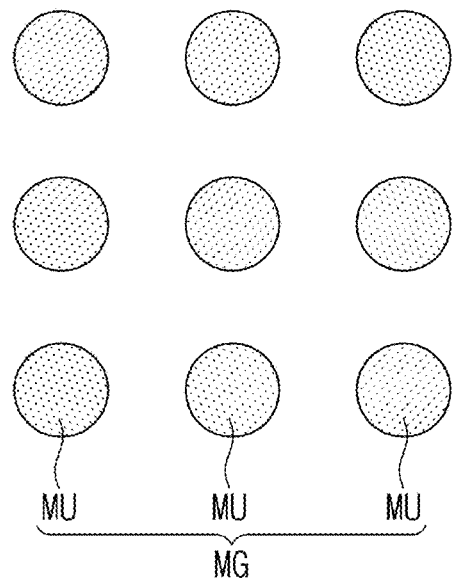
Figure 9H:
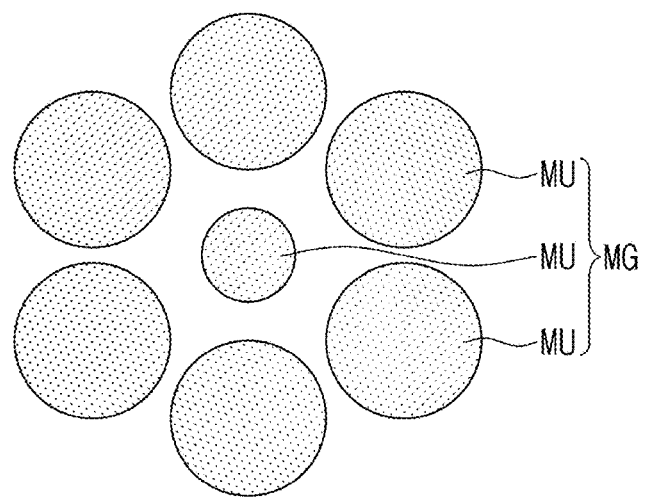

Referring to FIGS. 9G and 9H, the meta-material group MG may include three or more meta-material unit elements MU. Referring to FIG. 9G, a top surface of each of the meta-material unit elements MU may have a circular shape or an elliptical shape, and the meta-material unit elements MU may have the same size. The meta-material unit elements MU may be arranged with a constant period and may be aligned in two directions crossing each other.

Referring to FIG. 9H, a top surface of each of the meta-material unit elements MU may have a circular shape or an elliptical shape. One of the meta-material unit elements MU may be disposed at the center of the meta-material group MG, and the others may surround the meta-material unit element disposed at the center. The size of one of the meta-material unit elements MU disposed at the center may be different from the size of each of the others.

The meta-material group MG and the meta-material unit elements MU of FIGS. 9A to 9H are merely exemplary, and thus, the embodiment of the inventive concept is not limited thereto. For example, each of the meta-material group MG or the meta-material unit elements MU may have a structure having a geometric period and also may have a geometric period that is repeated itself. In addition, each of the meta-material group MG and the meta-material unit elements MU of FIGS. 9A to 9H may have quantum dots that emit light.

FIGS. 10A to 13A are perspective views for explaining an operation of the biosensor according to embodiment of the inventive concept. FIGS. 10B to 13B are pictures illustrating a diffraction pattern of the optical structure of the biosensor according to embodiments of the inventive concept Referring to FIGS. 10A and 10B, fifth incident light IL5 may be irradiated to the optical structure 30. The fifth incident light IL5 may be irradiated in the third direction D3 from a bottom surface of the substrate 10 toward the optical structure 30. The fifth incident light IL5 may be irradiated toward any one of the meta-material groups MG.

The fifth incident light IL5 may be diffracted by the meta-material unit elements MU of the meta-material groups MG and may be emitted as fifth emission light EL5. The fifth emission light EL5 may be emitted in the third direction D3 from the top surface of the substrate 10 toward the cover 50. The fifth emission light EL5 may be emitted from one of the meta-material groups MG.

Figure 10A:
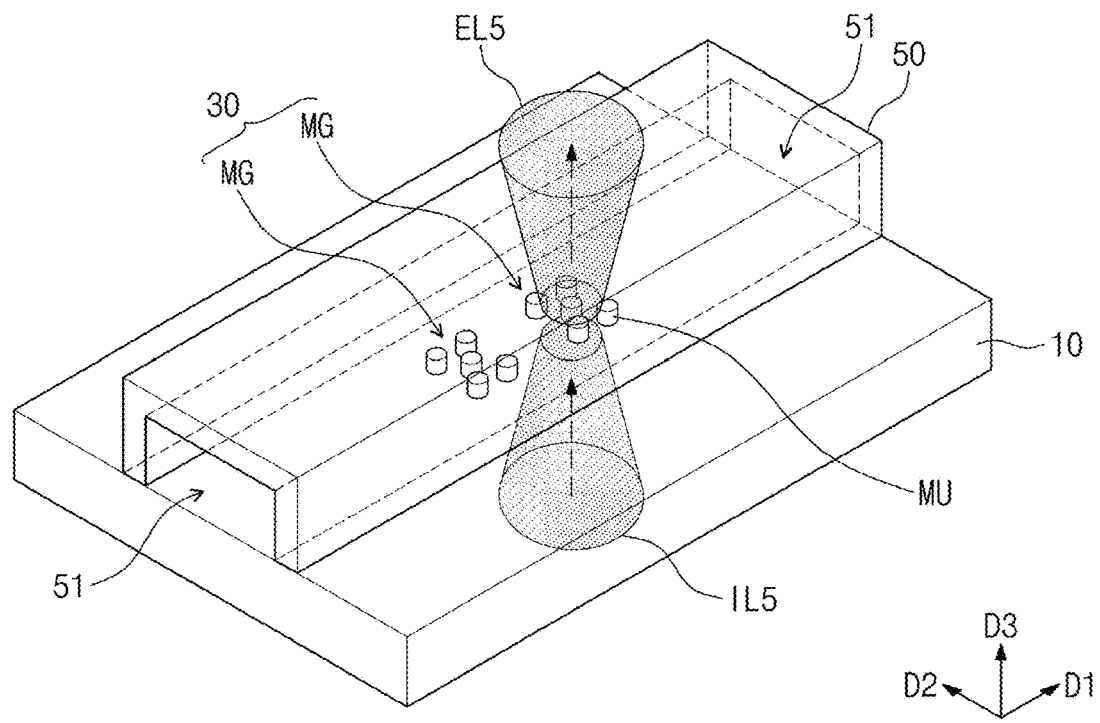
Figure 10B:
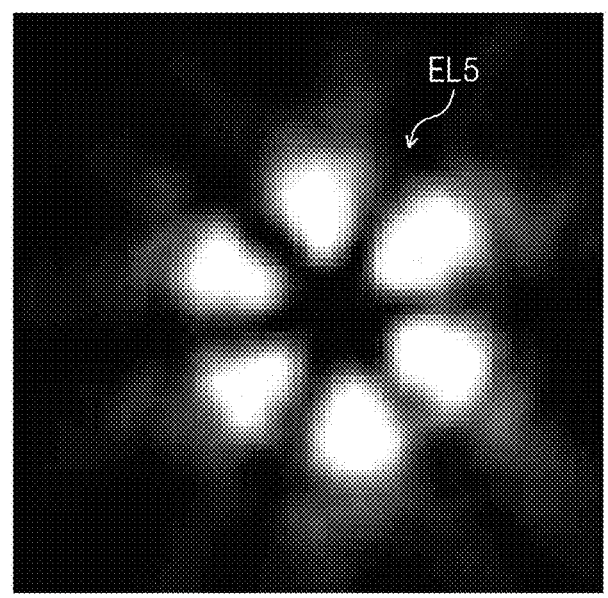

The fifth emitted light EL5 may be measured by a CMOS camera or a CCD camera on the optical structure 30, and a diffraction pattern of FIG. 10B represents the fifth emission light EL5. Hereinafter, for convenience of description, descriptions of the contents that are substantially the same as those described with reference to FIGS. 10A and 10B will be omitted, and differences will be described in detail.

Figure 11A:
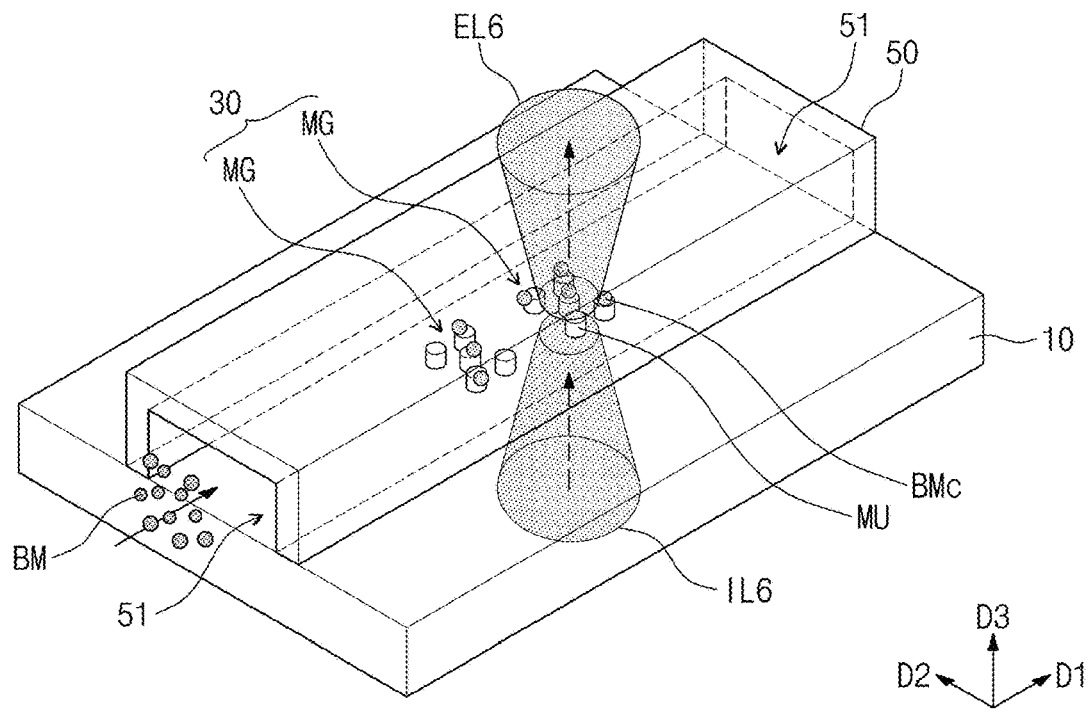
Figure 11B:
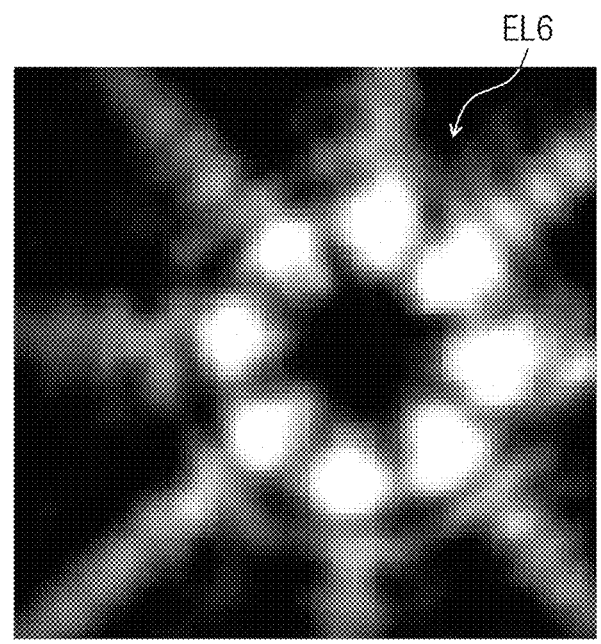

Referring to FIGS. 11A and 11B, a fluid including biomaterials BM may travel in the first direction D1 through the channel 51 of the cover 50. The biomaterials BM may include, for example, proteins, disease diagnosis-related biomarkers, viruses, bacteria, and the like. At least some of the biomaterials BM may be captured on the meta-material unit elements MU of the optical structure 30.

Thereafter, sixth incident light IL6 may be irradiated to the optical structure 30, and sixth emission light EL6 may be emitted from the optical structure 30. The sixth incident light IL6 may have substantially the same wavelength and intensity as the fifth incident light IL5.

Due to the biomaterials BM captured on the meta-material unit elements MU, the diffraction pattern (the diffraction pattern of the sixth emission light EL6) of FIG. 11B may be different from the diffraction pattern (the fifth emission light EL5) of FIG. 10B.

Figure 12A:
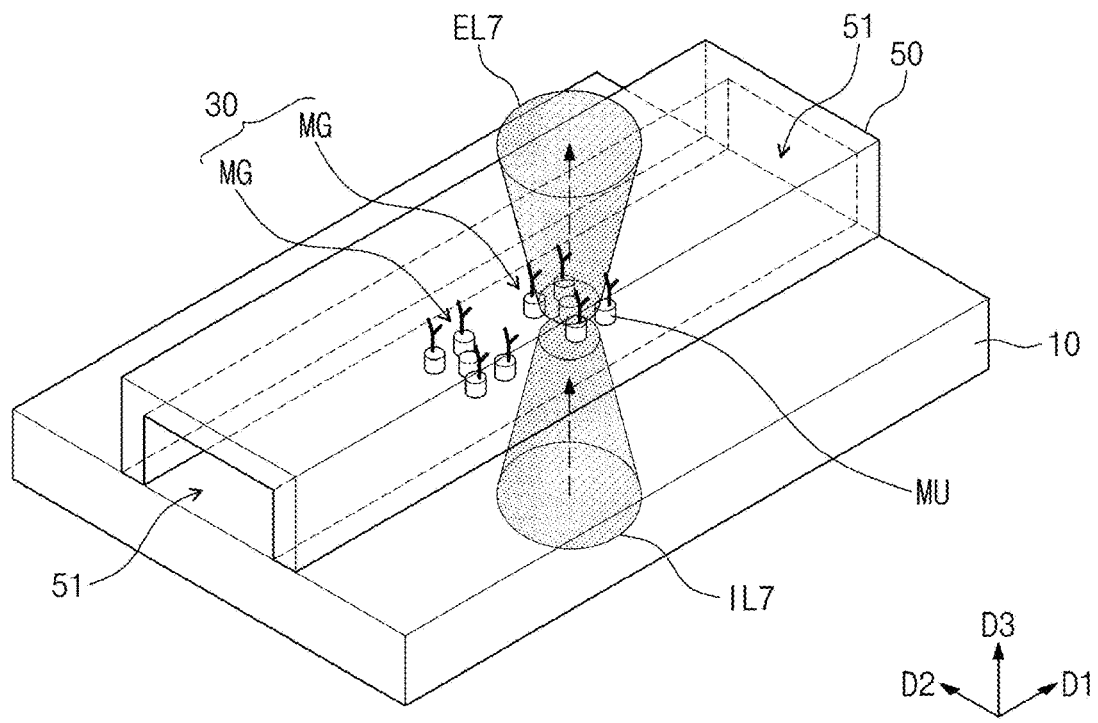
Figure 12B:
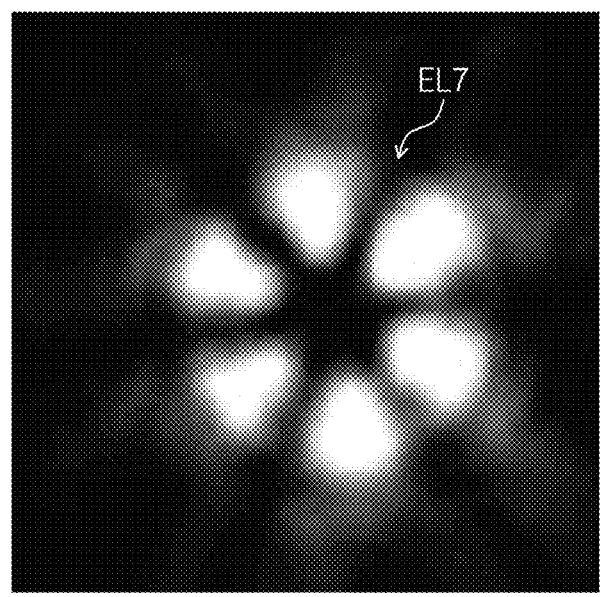

Referring to FIGS. 12A and 12B, the biosensor according to the inventive concept may further include a plurality of antibodies AB provided on the optical structure 30. Specifically, the antibodies AB may be provided on the top surface of each of the meta-material unit elements MU. The antibodies AB may be arranged along the first direction D1 on the top surface of the optical structure 30 and may be spaced apart from each other in the first direction D1. For example, the antibodies AB may be arranged in two rows on the top surface of the optical structure 30, and the rows may be spaced apart from each other in the second direction D2. Each of the antibodies AB may have, for example, a Y-shape.

Seventh incident light IL7 may be irradiated to the optical structure 30 provided with the antibodies AB on a top surface thereof, and seventh emission light EL7 may be emitted from the optical structure 30. The seventh incident light IL7 may have substantially the same wavelength and intensity as each of the fifth and sixth incident lights IL5 and IL6. A diffraction pattern (a diffraction pattern of the seventh emission light EL7) of FIG. 12B may be similar to the diffraction pattern (the diffraction pattern of the fifth emission light EL5) of FIG. 10B.

Figure 13A:
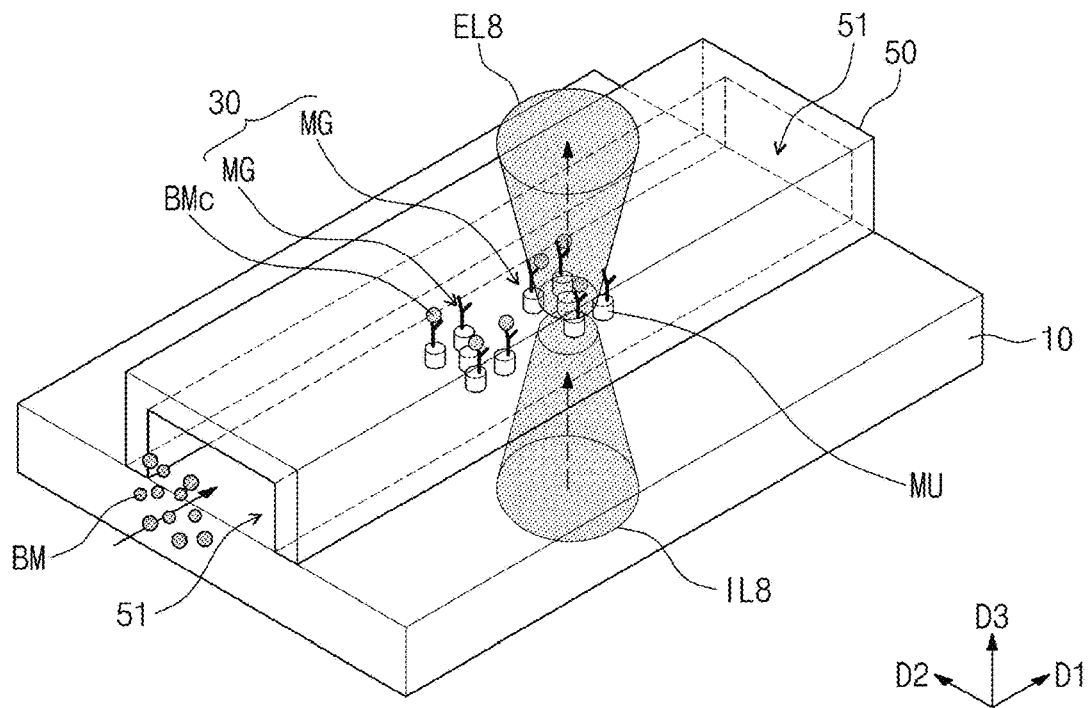
Figure 13B:
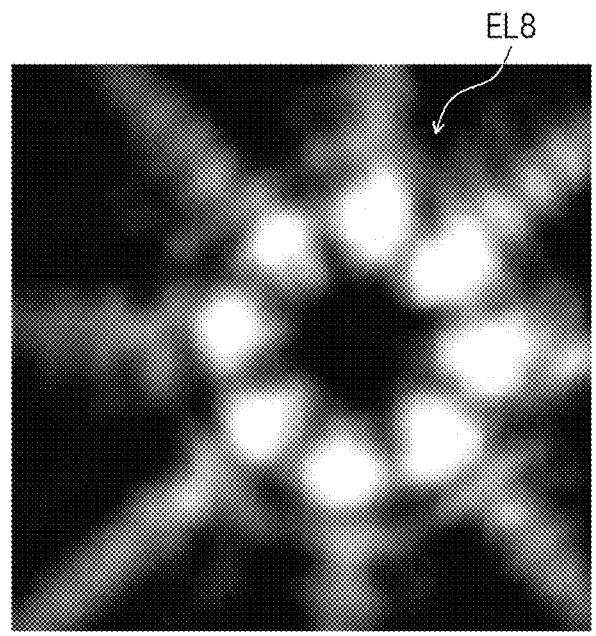

Referring to FIGS. 13A and 13B, a fluid including the biomaterials BM may travel in the first direction D1 through the channel 51 of the cover 50. At least some of the biomaterials BM may be captured on the antibodies AB on the optical structure 30 (or the meta-material unit elements MU of the optical structure 30).

Thereafter, eighth incident light IL8 may be irradiated to the optical structure 30, and an eighth emission light EL8 may be emitted from the optical structure 30. The eighth incident light IL8 may have substantially the same wavelength and intensity as each of the fifth to seventh incident light IL5, IL6, and IL7.

Due to the biomaterials BM captured on the antibodies AB (or the meta-material unit elements MU), the diffraction pattern (the diffraction pattern of the eighth emission light EL8) of FIG. 13B may be different from the diffraction pattern (the diffraction pattern of the seventh emission light EL7) of FIG. 12B.

FIGS. 14A to 17A are perspective views for explaining an operation of the biosensor according to embodiment of the inventive concept. FIGS. 14B to 15B are pictures illustrating an emission pattern of the optical structure of the biosensor according to embodiments of the inventive concept, and FIGS. 16B to 17B are pictures illustrating a diffraction pattern of the optical structure of the biosensor according to embodiments of the inventive concept. Specifically, FIGS. 14A to 17A illustrate a plurality of optical structures 30 or a plurality of meta-material groups MG arranged in an array form, through which a large-capacity sample may be inspected.

Figure 14A:
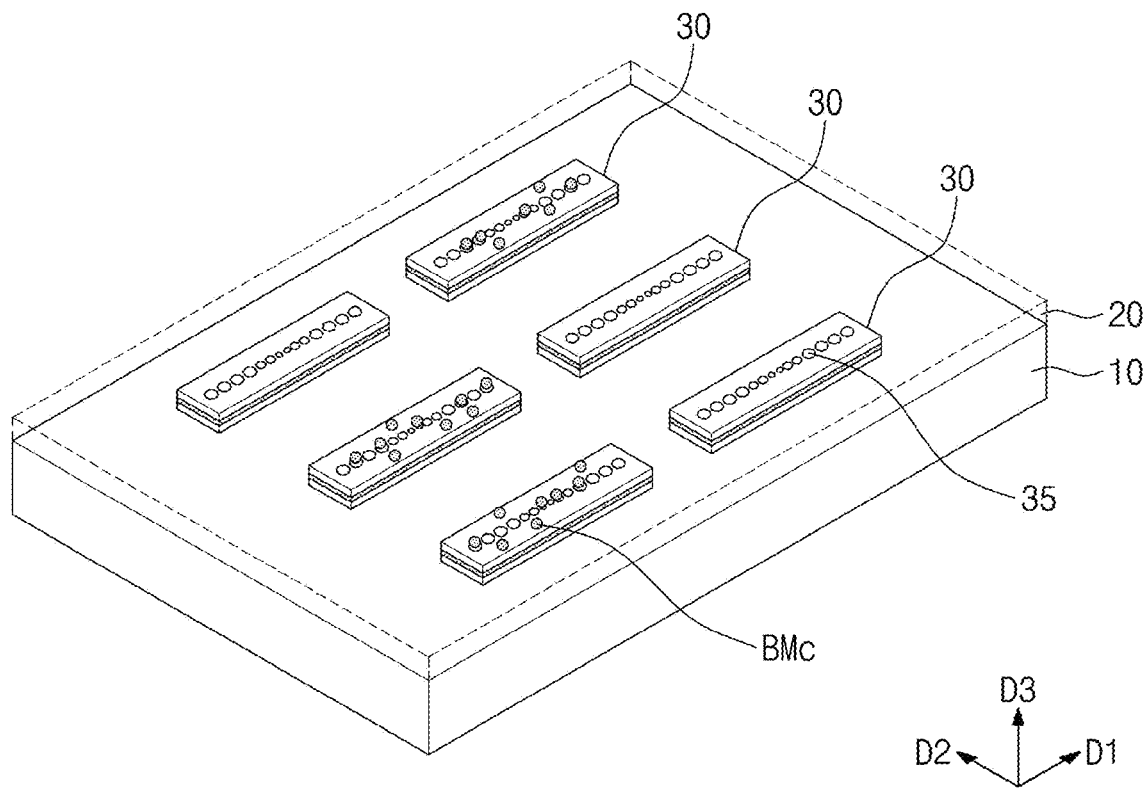
Figure 14B:
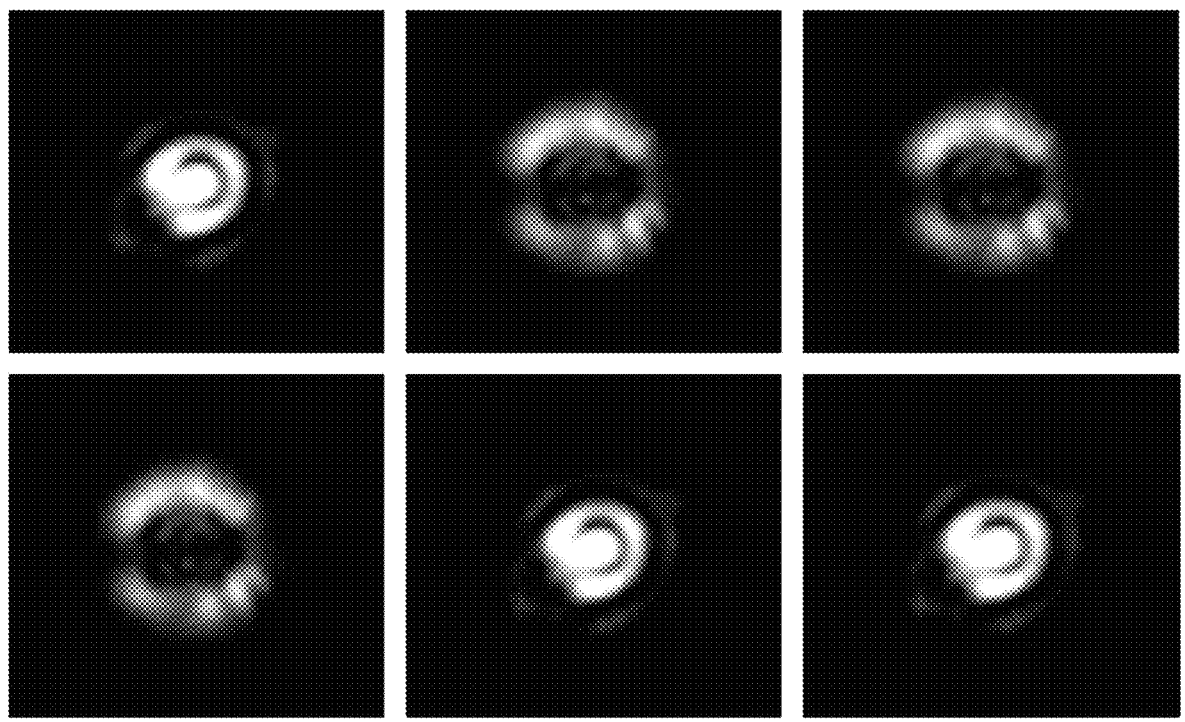

Referring to FIGS. 14A and 14B, the biosensor according to the inventive concept may include a substrate 10 and a plurality of optical structures 30 arranged on the substrate 10. Each of the optical structures 30 may be substantially the same as the optical structure 30 described with reference to FIGS. 1 and 2. The optical structures 30 may be arranged along the first direction D1 and the second direction D2. The optical structures 30 arranged along the first direction D1 may be spaced apart from each other in the first direction D1, and sidewalls of the optical structures 30 may be aligned with each other. The optical structures 30 arranged along the second direction D2 may be spaced apart from each other in the second direction D2, and sidewalls of the optical structures 30 may be aligned with each other. However, this is merely exemplary, and the embodiment of the inventive concept is not limited thereto. For example, an arrangement method of the plurality of optical structures 30 may be different from those shown above.

The biosensor according to the inventive concept may further include a dielectric layer 20 that covers a top surface of the substrate 10 and exposes a top surface of each of the optical structures 30. The dielectric layer 20 may cover a sidewall of each of the optical structures 30. A top surface of the dielectric layer 20 may be, for example, substantially coplanar with the top surface of each of the optical structures 30.

When a fluid flows through each of the optical structures 30, the biomaterials BM may be captured on at least some of the optical structures 30. Due to the biomaterials BM captured in the nanoholes 35 of the optical structures 30, the optical structures 30 on which the biomaterials BM are captured may have an emission pattern different from that of each of the optical structures 30 having no biomaterials BM. The emission pattern of FIG. 14B represents emission patterns generated from the plurality of optical structures 30.

Figure 15A:
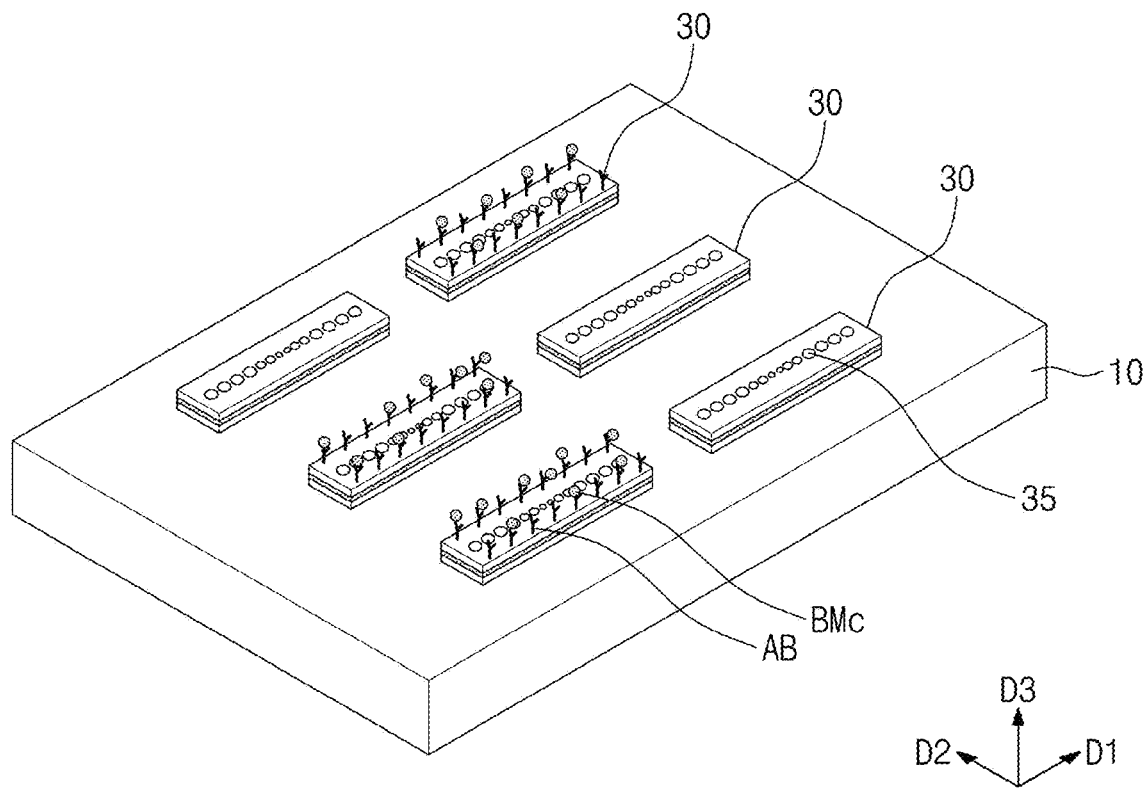
Figure 15B:
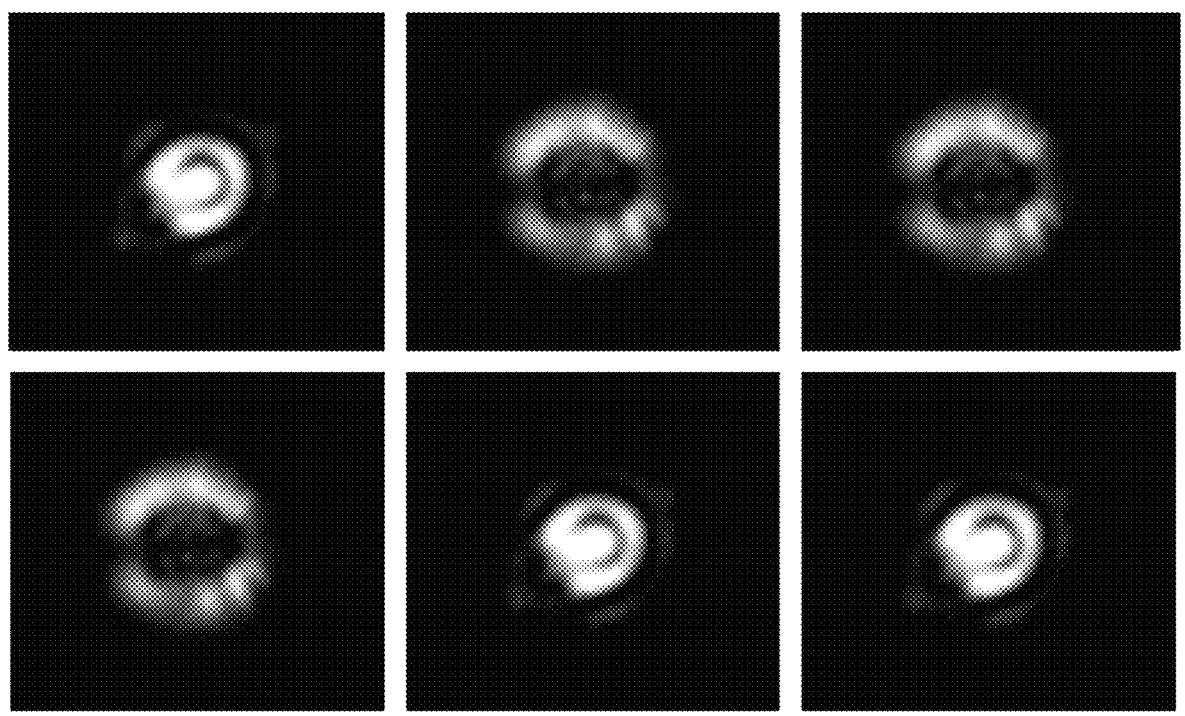

Referring to FIGS. 15A and 15B, a plurality of antibodies AB may be provided on at least some of the optical structures 30 in addition to those described with reference to FIGS. 14A and 14B. The arrangement method of the antibodies AB may be substantially the same as described with reference to FIG. 6A.

When a fluid flows through each of the optical structures 30, the biomaterials BM may be captured on the antibodies AB on at least some of the optical structures 30 (or in the nanoholes 35 of at least some of the optical structures 30). Due to the biomaterials BM captured on the antibodies AB (or in the nanoholes 35), each of the optical structures 30 on which the biomaterials BM are captured may have an emission pattern different from that of each of the optical structures 30 having no biomaterials BM. The emission pattern of FIG. 15B represents emission patterns generated from the plurality of optical structures 30.

Figure 16A:
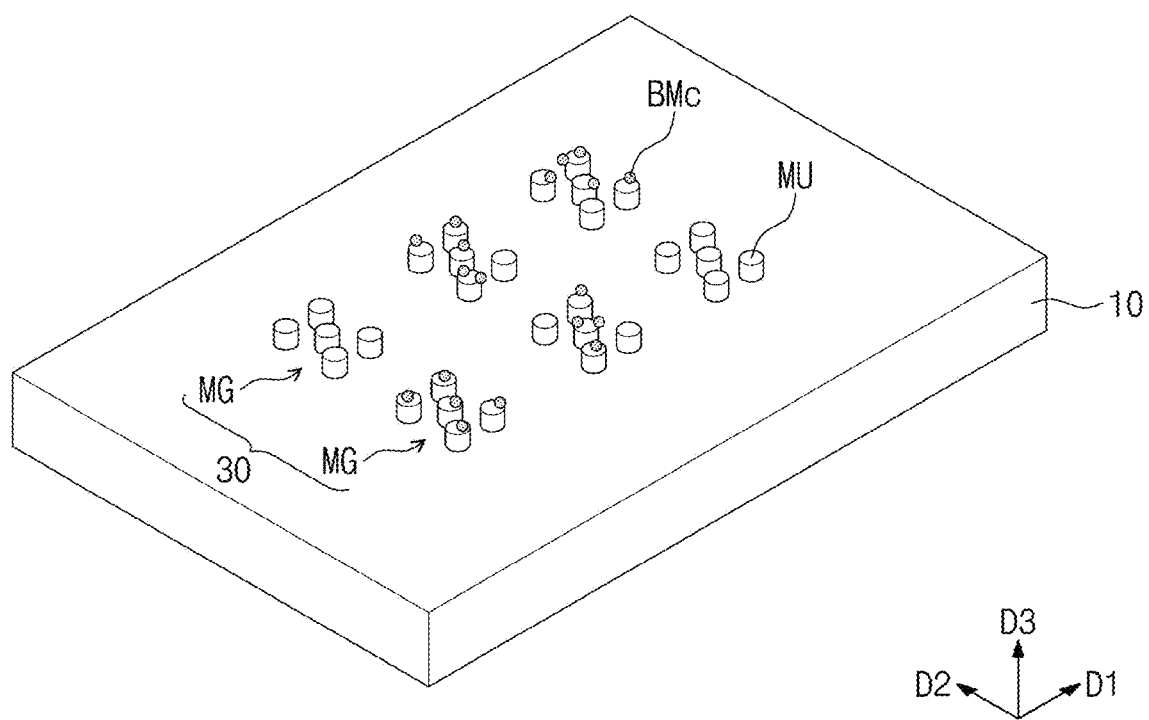
Figure 16B:
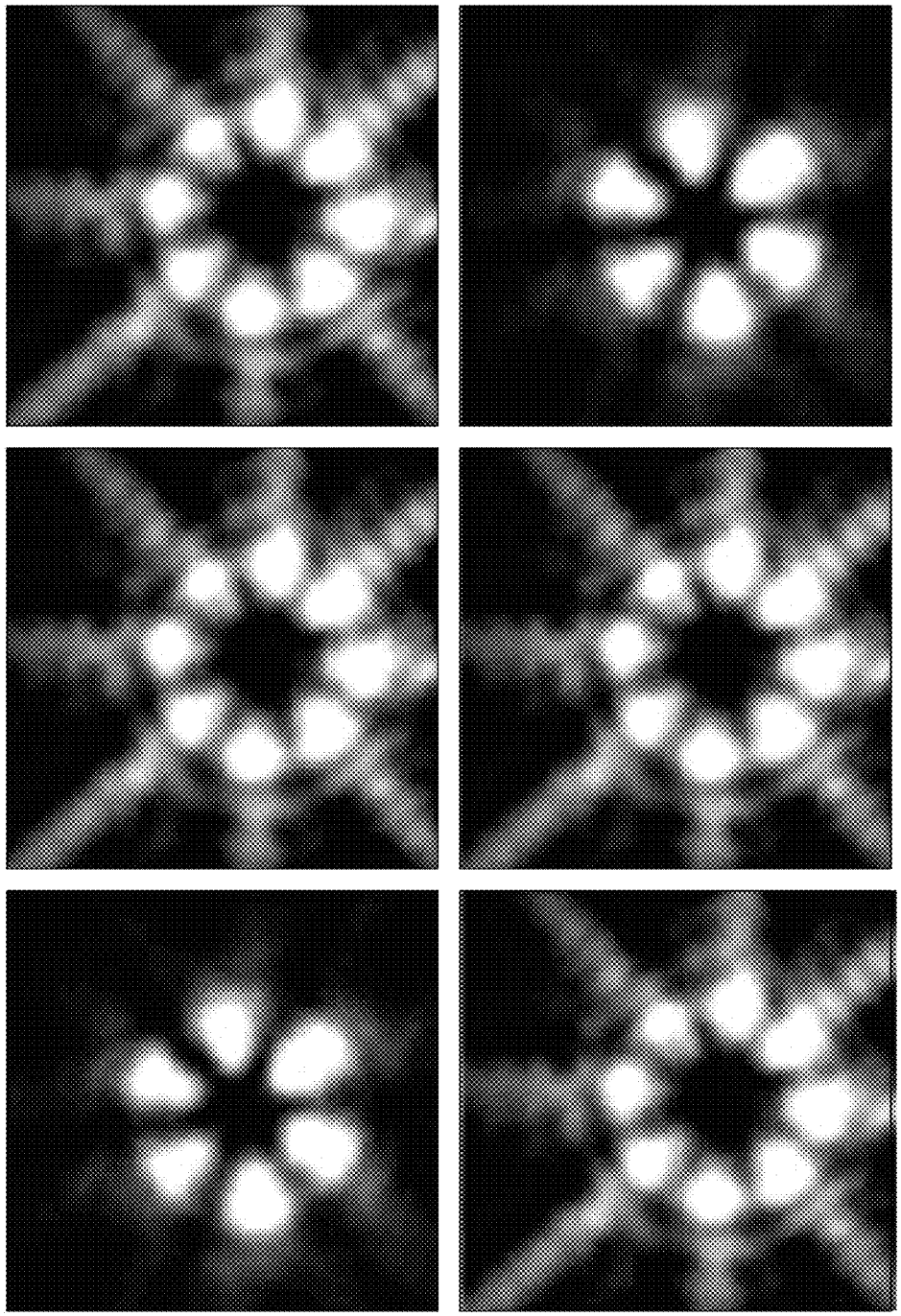

Referring to FIGS. 16A and 16B, the biosensor according to the inventive concept may include a substrate 10 and an optical structure 30 on the substrate 10. The optical structure 30 may include a plurality of meta-material groups MG. Each of the meta-material groups MG may include a plurality of meta-material unit elements MU. The meta-material groups MG may be arranged in the first direction D1 and the second direction D2. The meta-material groups MG arranged along the first direction D1 may be spaced apart from each other in the first direction D1, and the meta-material groups MG arranged along the second direction D2 may be separated apart from each other in the second direction D2. However, this is merely exemplary, and the embodiment of the inventive concept is not limited thereto. For example, the arrangement method of the plurality of meta-material groups MG may be different from those shown above.

When a fluid flows through each of the meta-material groups MG, the biomaterials BM may be captured on at least some of the meta-material groups MG. Due to the biomaterials BM captured on the meta-material unit elements MU of the meta-material groups MG, the meta-material groups MG on which the biomaterials BM are captured are the biomaterials BM may have a diffraction pattern different from that of the meta-material groups (MG) having no biomaterials BM. FIG. 16B illustrates a diffraction pattern generated from the plurality of meta-material groups MG.

Figure 17A:
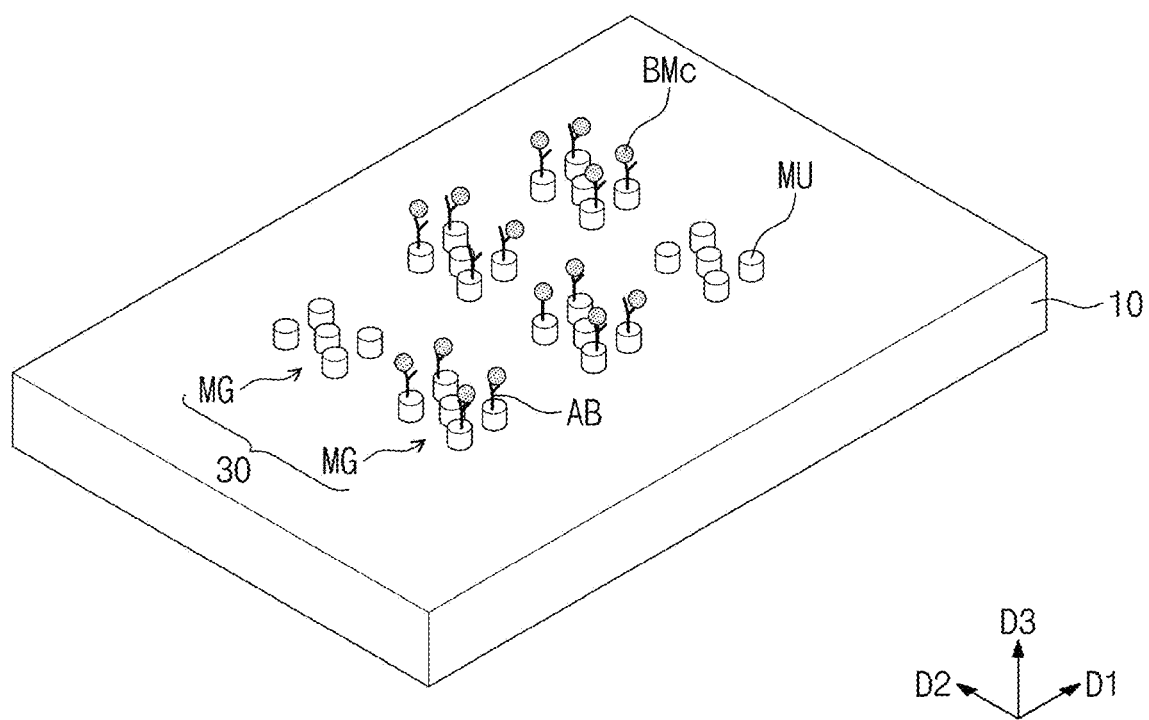
Figure 17B:
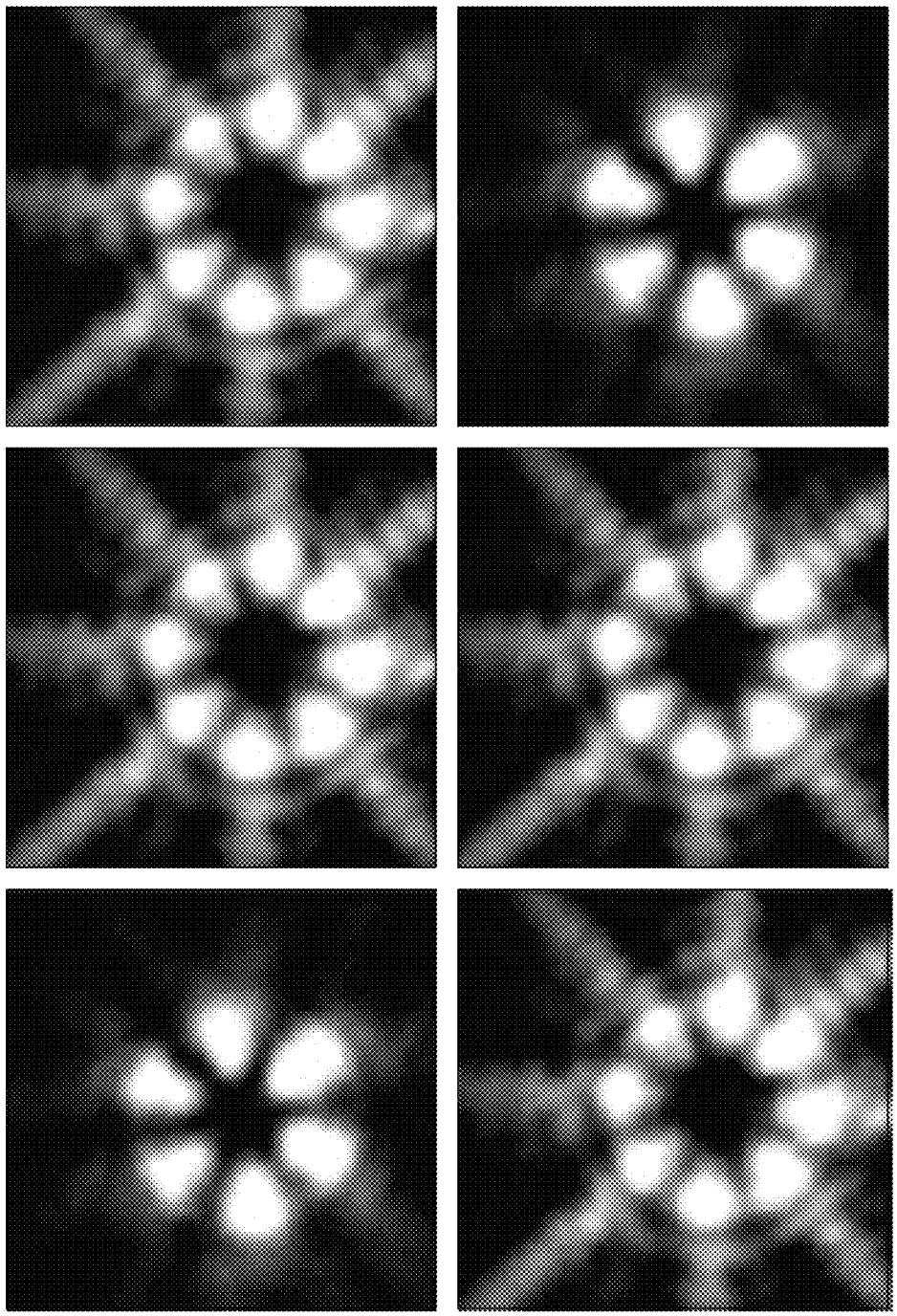

Referring to FIGS. 17A and 17B, in addition to those described with reference to FIGS. 16A and 16B, a plurality of antibodies AB may be provided on at least some of the meta-material groups MG. The arrangement method of the antibodies AB may be substantially the same as described with reference to FIG. 12A.

When a fluid flows through each of the meta-material groups MG, the biomaterials BM may be captured on the antibodies AB (or at least some of the meta-material groups MG) on at least some of the meta-material groups MG are meta-material unit elements MU. Due to the antibodies AB (or the biomaterials BM captured on the meta-material unit elements MU of the meta-material groups MG), the meta-material groups MG on which the biomaterials BM are captured are the biomaterials BM may have a diffraction pattern different from that of the meta-material groups (MG) having no biomaterials BM. FIG. 17B illustrates a diffraction pattern generated from the plurality of meta-material groups MG.

Figure 18:
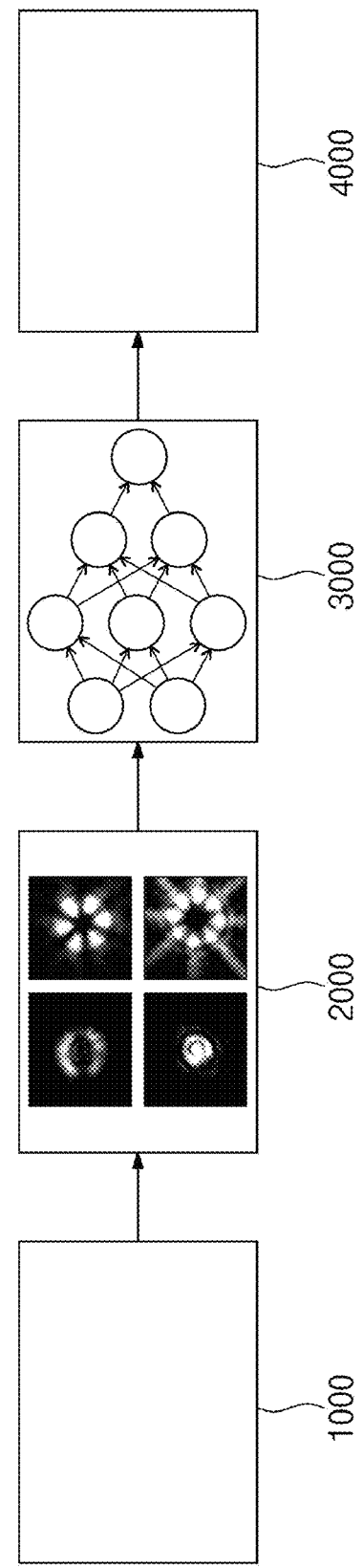
FIG. 18 is a conceptual view for explaining a biosensor and a method for determining presence or absence of a biomaterial using the biosensor according to embodiments of the inventive concept.

FIG. 18 is a conceptual view for explaining a biosensor and a method for determining presence or absence of a biomaterial using the biosensor according to embodiments of the inventive concept.

Referring to FIG. 18, the biosensor according to the inventive concept may include a measuring unit 1000, a data storage unit 2000, a data learning unit 3000, and a display unit 4000.

The measuring unit 1000 includes a substrate 10, an optical structure 30, a cover 50, and a CMOS camera or CCD camera that measures light emitted from the optical structure 30, which are described with reference to FIGS. 1 and 2, and thus may measure (photograph) an emission pattern or diffraction pattern of emitted light of the biosensor.

The data storage unit 2000 may store data measured by the measuring unit 1000. Specifically, the data storage unit 2000 may store data including the emission pattern or the diffraction pattern of the emitted light, which is measured by the measuring unit 1000.

The data learning unit 3000 may perform machine learning through the data transmitted from the data storage unit 2000. Specifically, the data learning unit 3000 may be trained to determine a presence or absence of the biomaterial and/or the number of biomaterials through a change in light information such as a resonance wavelength, a phase, and/or polarization of the emission patterns or diffraction patterns.

An algorithm of the data learning unit 3000 may be, for example, one of a neural network (NN), a convolutional neural network (CNN), a graph neural network (GNN), and a Gaussian process regression (GPR).

The display unit 4000 may visualize and display information such as the presence or absence of the biomaterial and/or the number of biomaterials determined by the data learning unit 3000.

The biosensor according to the inventive concept may use the precise nano-optical structure having the small size without various optical components such as a light source, a spectrometer, a detector, or a filter and may easily and effectively determine the presence or absence of the biomaterial through the change in optical information such as a resonance wavelength, a phase, and/or polarization.

The biosensor according to the inventive concept may use the precise nano-optical structure having the small size and may easily and effectively determine the presence or absence of the biomaterial through the change in optical information such as a resonance wavelength, a phase, and/or polarization.

Although the embodiment of the inventive concept is described with reference to the accompanying drawings, those with ordinary skill in the technical field of the inventive concept pertains will be understood that the present disclosure can be carried out in other specific forms without changing the technical idea or essential features. Therefore, the above-disclosed embodiments are to be considered illustrative and not restrictive.

What is claimed is:

1. A biosensor comprising:
a substrate;
an optical structure provided on the substrate and including a plurality of nanoholes; and
a cover provided on the substrate and having a bridge shape that is in contact with a top surface of the substrate at both sides of the optical structure,
wherein the cover has a channel extending in a first direction,
the optical structure is provided inside the channel,
the optical structure is configured to capture biomaterials that travel through the channel,
the channel has an inlet opening and an outlet opening exposing both sides of the optical structure to outside of the channel,
each of the inlet opening and the outlet opening has a height greater than that of the optical structure, and
a diameter and a period of each of the nanoholes decrease in the first direction from one end of the optical structure toward a central portion of the optical structure and increase in the first direction from the central portion toward the other end of the optical structure, which faces the one end.

2. The biosensor of claim 1, wherein the optical structure comprises a lower layer, an active layer, and an upper layer, which are sequentially stacked on the substrate,
wherein the active layer is interposed between the lower layer and the upper layer,
wherein the optical structure comprises a Group III-V semiconductor material,
wherein the lower layer and the upper layer comprise the same semiconductor material, and
wherein the active layer comprises a semiconductor material different from that of each of the lower layer and the upper layer.

3. The biosensor of claim 2, wherein the plurality of nanoholes of the optical structure pass through the lower layer, the active layer, and the upper layer.

4. The biosensor of claim 3, wherein a first length of the optical structure in the first direction is about 3 μm or more, a second length of the optical structure in the second direction is about 200 nm to about 700 nm, and a thickness of the optical structure in a third direction perpendicular to the first and second directions is about 100 nm to about 300 nm, and
wherein the diameter of each of the nanoholes is about 100 nm to 500 nm and each of the nanoholes has a circular shape.

5. The biosensor of claim 1, further comprising a CMOS camera or CCD camera provided on the optical structure.

6. The biosensor of claim 1, wherein the optical structure comprises a lower layer on the substrate and an upper layer on a partial area of the lower layer,
wherein the optical structure has the plurality of nanoholes passing through the lower layer to expose the top surface of the substrate.

7. The biosensor of claim 6, wherein the upper layer comprises one of a semiconductor material or transition metal dichalcogenide, graphene, and hexagonal boron nitride (hBN).

8. The biosensor of claim 1, further comprising a plurality of antibodies provided on the optical structure,
wherein the antibodies are arranged along the first direction on a top surface of the optical structure, and
the antibodies are configured to capture the biomaterials that travel through the channel.

9. The biosensor of claim 1, wherein the optical structure is provided in plurality, and the optical structures are arranged along the first direction and a second direction crossing the first direction.

10. A biosensor comprising:
a substrate;
an optical structure having a bar shape extending in a first direction on the substrate; and
a cover provided on the substrate and having a bridge shape that is in contact with a top surface of the substrate at both sides of the optical structure,
wherein the cover has a channel extending in the first direction, the channel having an inlet opening and an outlet opening that expose both sides of the optical structure to outside of the channel, each of the inlet opening and the outlet opening having a height greater than that of the optical structure,
the optical structure is provided inside the channel, and
the optical structure comprises:
a lower layer on the substrate;
an upper layer on the lower layer; and
an active layer interposed between the lower layer and the upper layer,
wherein the optical structure has a plurality of nanoholes passing through the lower layer, the active layer, and the upper layer, and
wherein a diameter and a period of each of the nanoholes decrease in the first direction from one end of the optical structure toward a central portion of the optical structure and increase in the first direction from the central portion toward the other end of the optical structure, which faces the one end.

11. The biosensor of claim 10, wherein the active layer has quantum dots configured to control photons of laser light emitted from the optical structure, and
the active layer comprises a material different from that of each of the lower layer and the upper layer.

12. The biosensor of claim 10, wherein the optical structure is provided in plurality,
the optical structures are arranged along the first direction and a second direction crossing the first direction,
the optical structures arranged along the first direction are spaced apart from each other in the first direction, and sidewalls of the optical structures are aligned with each other, and
the optical structures arranged along the second direction are spaced apart from each other in the second direction, and sidewalls of the optical structures are aligned with each other.

13. A biosensor comprising:
a measuring unit configured to measure an emission pattern or a diffraction pattern;
a data storage unit configured to store data comprising the emission pattern or the diffraction pattern measured in the measuring unit;
a data learning unit is configured to perform machine learning through the data transmitted from the data storage unit and determine a presence or absence of the biomaterial and the number of biomaterials through the data; and
a display unit configured to visualize information determined by the data learning unit,
wherein the measuring unit comprises:
a substrate;
an optical structure provided on the substrate; and
a cover having a bridge shape that is in contact with a top surface of the substrate at both sides of the optical structure,
wherein the cover has a channel extending in a first direction, the optical structure is provided inside the channel, and the optical structure is configured to capture biomaterials that travel through the channel,
wherein the optical structure includes a central portion and end portions, the central portion corresponding to a resonator region configured to generate resonance, the end portions corresponding to mirror regions configured to reflect light,
wherein the optical structure has a plurality of nanoholes passing therethrough, and
wherein a diameter and a period of each of the nanoholes decrease in the first direction from one end of the optical structure toward the central portion of the optical structure and increase in the first direction from the central portion toward the other end of the optical structure, which faces the one end.

14. The biosensor of claim 13, wherein the data learning unit is trained to determine a presence or absence of the biomaterial and the number of biomaterials through a change in at least one of a resonance wavelength, a phase, or polarization.

15. The biosensor of claim 13, wherein the optical structure comprises:
a lower layer on the substrate;
an upper layer on the lower layer; and
an active layer interposed between the lower layer and the upper layer,
wherein the optical structure has a plurality of nanoholes passing through the lower layer, the active layer, and the upper layer.

16. The biosensor of claim 13, wherein the optical structure is provided in plurality, and
the optical structures are arranged along the first direction and a second direction crossing the first direction.

* * * * *